United States Patent
Bonnert et al.

(10) Patent No.: US 6,875,868 B2
(45) Date of Patent: Apr. 5, 2005

(54) PTERIDINE COMPOUNDS FOR THE TREATMENT OF PSORIASIS

(75) Inventors: Roger Bonnert, Loughborough (GB); Stewart Gardiner, Loughborough (GB); Fraser Hunt, Loughborough (GB); Iain Walters, Loughborough (GB)

(73) Assignee: AstraZeneca AB (SE)

( * ) Notice: Subject to any disclaimer, the term of this patent is extended or adjusted under 35 U.S.C. 154(b) by 11 days.

(21) Appl. No.: 10/204,814
(22) PCT Filed: Feb. 20, 2001
(86) PCT No.: PCT/SE01/00374
§ 371 (c)(1),
(2), (4) Date: Aug. 22, 2002
(87) PCT Pub. No.: WO01/62758
PCT Pub. Date: Aug. 30, 2001

(65) Prior Publication Data
US 2003/0055250 A1 Mar. 20, 2003

(30) Foreign Application Priority Data
Feb. 23, 2000 (GB) .............................. 0004128

(51) Int. Cl.[7] ............................................ C07D 487/04
(52) U.S. Cl. ...................................................... 544/258
(58) Field of Search ........................................ 544/258

(56) References Cited

FOREIGN PATENT DOCUMENTS

| | | |
|---|---|---|
| EP | 0 293 078 A1 | 11/1988 |
| EP | 0 447 324 A1 | 9/1991 |
| WO | WO 00/39129 | 7/2000 |
| WO | WO 00/45800 | 8/2000 |
| WO | WO 01/19825 A1 | 3/2001 |

OTHER PUBLICATIONS

Patent Abstracts of Japan, abstract of JP–5–202047 A (Chugai Pharmaceut. Co. Ltd.) Aug. 10, 1993.
Manfred Ott et al., "Zur Synthese des 4–Amino–7–oxo–7, 8–dihydropteridin–N–8–beta–D–ribofuranosids—ein strukturanaloges Nucleosid des Adenosins", vol. 107, Chem.Ber., 339–361 (1974).
Manfred Ott et al., "4–Amino–7, 8–Dihydro–2–(Methylmercapto)–8–beta, –D–ribofuranosylpteridin–7– One, Modified Fusion Reaction with Trimethylsilylated Pteridine Derivatives", vol. 2, Nucl. Acid. Chem., 735–739 (1978).
Leonidas Kiriasis et al., "Synthesis and Properties of New Pteridine Nucleosides", vol. 4, Dev. Biochem., 49–53 (1978).

*Primary Examiner*—Richard L. Raymond
(74) *Attorney, Agent, or Firm*—Fish & Richardson, P.C.

(57) ABSTRACT

The invention provides pteridine compounds of formula (I), processes and intermediates used in their preparation, pharmaceutical compositions containing them and their use in therapy. Formula (I) in which A is a group of formula (a) or (b).

7 Claims, No Drawings

PTERIDINE COMPOUNDS FOR THE TREATMENT OF PSORIASIS

CROSS REFERENCE TO RELATED APPLICATIONS

The present application is a national phase application under 35 U.S.C. Section 371 filed from International Patent Application PCT/SE01/00374, filed 20 Feb. 2001, which claims priority to United Kingdom patent application Serial No. 0004128.5, filed 23 Feb. 2000. The contents of these applications are incorporated herein by reference in their entirety.

The present invention relates to certain heterocyclic compounds, processes and intermediates used in their preparation, pharmaceutical compositions containing them and their use in therapy.

Chemokines play an important role in immune and inflammatory responses in various diseases and disorders, including asthma and allergic diseases, as well as autoimmune pathologies such as rheumatoid arthritis and atherosclerosis. These small secreted molecules are a growing superfamily of 8–14 kDa proteins characterised by a conserved cysteine motif. At the present time, the chemokine superfamily comprises three groups exhibiting characteristic structural motifs, the C—X—C, C—C and C—X$_3$—C families. The C—X—C and C—C families have sequence similarity and are distinguished from one another on the basis of a single amino acid insertion between the NH-proximal pair of cysteine residues. The C—X$_3$—C family is distinguished from the other two families on the basis of having a triple amino acid insertion between the NH-proximal pair of cysteine residues.

The C—X—C chemokines include several potent chemoattractants and activators of neutrophils such as interleukin-8 (IL-8) and neutrophil-activating peptide 2 (NAP-2).

The C—C chemokines include potent chemoattractants of monocytes and lymphocytes but not neutrophils. Examples include human monocyte chemotactic proteins 1–3 (MCP-1, MCP-2 and MCP-3), RANTES (Regulated on Activation, Normal T Expressed and Secreted), eotaxin and the macrophage inflammatory proteins 1α and 1β (MIP-1α and MIP-1β).

The C—X$_3$—C chemokine (also known as fractalkine) is a potent chemoattractant and activator of microglia in the central nervous system (CNS) as well as of monocytes, T cells, NK cells and mast cells.

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and CX$_3$CR1 for the C—X$_3$—C family. These receptors represent good targets for drug development since agents which modulate these receptors would be useful in the treatment of disorders and diseases such as those mentioned above.

The present invention provides compounds of formula (I) and pharmaceutically acceptable salts or solvates thereof:

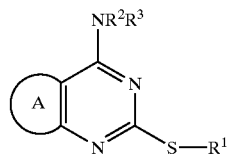

(I)

in which:
A is a group of formula (a) or (b):

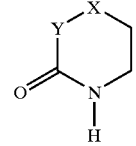

(a)

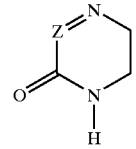

(b)

R$^1$ represents a C$_3$–C$_7$ carbocyclic, C$_1$–C$_8$ alkyl, C$_2$–C$_6$ alkenyl or C$_2$–C$_6$ alkynyl group, the latter four groups being optionally substituted by one or more substituent groups independently selected from halogen atoms, —OR$^4$, —NR$^5$R$^6$, —CONR$^5$R$^6$, —COOR$^7$, —NR$^8$COR$^9$, —SR$^{10}$, —SO$_2$R$^{10}$, —SO$_2$NR$^5$R$^6$, —NR$^8$SO$_2$R$^{10}$, an aryl or heteroaryl group both of which can be optionally substituted by one or more substituents independently selected from halogen atoms, cyano, nitro, —OR$^4$, —NR$^5$R$^6$, —CONR$^5$R$^6$, —COOR$^7$, —NR$^8$COR$^{10}$, —SR$^{10}$, —SO$_2$R$^{10}$, —SO$_2$NR$^5$R$^6$, —NR$^8$SO$_2$R$^{10}$, C$_1$–C$_6$ alkyl or trifluoromethyl groups;

R$^2$ represents hydrogen or a C$_3$–C$_7$ carbocyclic group, C$_1$–C$_8$ alkyl, C$_2$–C$_6$ alkenyl or C$_2$–C$_6$ alkynyl group, the latter four groups may be optionally substituted by one or more substituent groups independently selected from halogen atoms, —OR$^4$, —NR$^5$R$^6$ —CONR$^5$R$^6$, —COOR$^7$, —NR$^8$COR$^9$, —SR$^{10}$, —SO$_2$R$^{10}$, —SO$_2$NR$^5$R$^6$ or —NR$^8$SO$_2$R$^9$;

R$^3$ represents hydrogen or C$_2$–C$_6$ alkyl optionally substituted by one or more substituent groups independently selected from halogen atoms, phenyl, —OR$^{10}$ and —NR$^{11}$R$^{12}$; or R$^2$ and R$^3$ represent a 3–8 membered ring optionally containing one or more atoms selected from O, S, NR$^8$ and itself optionally substituted by C$_{1-3}$-alkyl, halogen or OR$^4$;

R$^4$ represents hydrogen, C$_1$–C$_6$ alkyl or a phenyl group the latter two of which may be optionally substituted by one or more substituent groups independently selected from halogen atoms, phenyl, —OR$^{11}$ and —NR$^{12}$R$^{13}$;

R$^5$ and R$^6$ independently represent a hydrogen atom or a C$_1$–C$_6$ alkyl or phenyl group the latter two of which may be optionally substituted by one or more substituent groups independently selected from halogen atoms, phenyl, —OR$^{14}$ and —NR$^{15}$R$^{16}$, —CONR$^{15}$R$^{16}$, —NR$^{15}$COR$^{16}$, —SO$_2$NR$^{15}$R$^{16}$, NR$^{15}$SO$_2$R$^{16}$ or R$^5$ and R$^6$ together with the nitrogen atom to which they are attached form a 4- to 7-membered saturated heterocyclic ring system optionally comprising a further heteroatom selected from oxygen and nitrogen atoms, which ring system may be optionally substituted by one or more substituent groups independently selected from phenyl, —OR$^{14}$, —COOR$^{14}$, —NR$^{15}$R$^{16}$, —CONR$^{15}$R$^{16}$, —NR$^{15}$COR$^{16}$, —SO$_2$NR$^{15}$R$^{16}$, NR$^{15}$SO$_2$R$^{16}$ or C$_1$–C$_6$ alkyl, itself optionally substituted by one or more substituents independently selected from halogen atoms and —NR$^{15}$R$^{16}$ and —OR$^{17}$ groups;

R$^{10}$ represents a C$_1$–C$_6$ alkyl or a phenyl group, each of which may be optionally substituted by one or more substituent groups independently selected from halogen atoms, phenyl, —OR$^{17}$ and —NR$^{15}$R$^{16}$;

X is O, S or NR$^8$;

Y is CR$^{18}$R$^{19}$;

Z is CR$^{20}$ where R$^{20}$ represents H, a C$_1$–C$_6$ alkyl or a phenyl group, each of which may be optionally substituted by one or more substituent groups independently selected from halogen atoms, phenyl, —OR$^{21}$ and —NR$^{22}$R$^{23}$, or an acyl group selected from CO$_2$R$^{21}$ or CONR$^{22}$R$^{23}$; and each of R$^7$, R$^8$, R$^9$, R$^{11}$, R$^{12}$, R$^{13}$, R$^{14}$R$^{15}$, R$^{16}$, R$^{17}$, R$^{18}$, R$^{19}$, R$^{21}$, R$^{22}$ and R$^{23}$ independently represent a hydrogen atom, C$_1$–C$_6$, alkyl, or a phenyl group.

In the context of the present specification, unless otherwise indicated, an alkyl or alkenyl group or an alkyl or alkenyl moiety in a substituent group may be linear or branched.

Aryl groups include phenyl and naphthyl. Heteroaryl is defined as a 5- or 6-membered aromatic ring optionally containing one or more heteroatoms selected from N, S, O. Examples include pyridine, pyrimidine, thiazole, oxazole, pyrazole, imidazole, furan.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.

Suitably the group R$^1$ represents a C$_3$–C$_7$ carbocyclic, C$_1$–C$_8$ alkyl, C$_2$–C$_6$ alkenyl or C$_2$–C$_6$ alkynyl group, the latter four groups may be optionally substituted by one or more substituent groups independently selected from halogen atoms, —OR$^4$, —NR$^5$R$^6$, —CONR$^5$R$^6$, —COOR$^7$, —NR$^8$COR$^9$, —SR$^{10}$, —SO$_2$R$^{10}$, —SO$_2$NR$^5$R$^6$, —NR$^8$SO$_2$R$^{10}$, an aryl or heteroaryl group both of which can be optionally substituted by one or more substituents independently selected from halogen atoms, cyano, nitro, —OR$^4$, —NR$^5$R$^6$, —CONR$^5$R$^6$, —COOR$^7$, —NR$^8$COR$^{10}$, —SR$^{10}$, —SO$_2$R$^{10}$, —SO$_2$NR$^5$R$^6$, —NR$^8$SO$_2$R$^{10}$, C$_1$–C$_6$ alkyl or trifluoromethyl groups. Substituents can be present on any suitable position of the R$^1$, aryl and heteroaryl groups, including nitrogen atoms of heteroaryl groups. Particularly advantageous compounds of formula (I) are those in which R$^1$ represents an optionally substituted benzyl group. More preferably R$^1$ represents benzyl or benzyl substituted by one or more C$_1$–C$_6$ alkyl, C$_1$–C$_6$ alkoxy, or halogen atoms, still more preferably benzyl substituted by two fluoro atoms, and most preferably benzyl substituted by two fluoro atoms which are ortho and meta to the benyl CH$_2$ linkage.

Suitably R$^2$ represents hydrogen or a C$_3$–C$_7$ carbocyclic group, C$_1$–C$_8$ alkyl, C$_2$–C$_6$ alkenyl or C$_2$–C$_6$ alkynyl group, the latter four groups may be optionally substituted by one or more substituent groups independently selected from halogen atoms, —OR$^4$, —NR$^5$R$^6$ —CONR$^5$R$^6$, —COOR$^7$, —NR$^8$COR$^9$, —SR$^{10}$, —SO$_2$R$^{10}$, —SO$_2$NR$^5$R$^6$ or —NR$^8$SO$_2$R$^9$, and R$^3$ represents hydrogen or C$_2$–C$_6$ alkyl optionally substituted by one or more substituent groups independently selected from halogen atoms, phenyl, —OR$^{10}$ and —NR$^{11}$R$^{12}$; or R$^2$ and R$^3$ represent a 3–8 membered ring optionally containing one or more atoms selected from O, S, NR$^8$ and itself optionally substituted by C$_{1-3}$-alkyl, halogen or OR$^4$;

Preferably one of R$^2$ and R$^3$ is hydrogen and the other is C$_3$–C$_4$ alkyl substituted by one or more hydroxy groups. More preferably one of R$^2$ and R$^3$ is hydrogen and the other is CH(CH$_3$)CH$_2$OH, CH(Et)CH$_2$OH, C(CH$_3$)$_2$CH$_2$OH or CH(CH$_2$OH)$_2$. When one of R$^2$ and R$^3$ is hydrogen and the other is CH(CH$_3$)CH$_2$OH or CH(Et)CH$_2$OH the resulting compounds of formula (I) are preferably in the form of the (R) isomer. Most preferably one of R$^2$ and R$^3$ is hydrogen and the other is CH(CH$_3$)CH$_2$OH.

When A is a group of formula (a), X represents O, S or NR$^8$. When X represents NR$^8$ then R$^8$ is preferably hydrogen or C$_{1-6}$ alkyl. Preferably X is S. Suitably Y is CR$^{18}$R$^{19}$, preferably Y is CH$_2$.

Preferably A is a group of formula (b) and Z is CR$^{20}$ most preferably Z is CH.

Particularly preferred compounds of the invention include:

4-[[(1R)-2-Hydroxy-1-methylethyl]amino]-2-[(phenylmethyl)thio]-6H-pyrimido[5,4-b][1,4]thiazin-7(8H)-one 2-[[(2,3-Difluorophenyl)methyl]thio]-4-[[(1R)-2-hydroxy-1-methylethyl]amino]-7(8H)-pteridinone 2-[[(2,3-Difluorophenyl)methyl]thio]-4-[[2-hydroxy-1-(hydroxymethyl)ethyl]amino]-7(8H)-pteridinone 2-[[(2,3-Difluorophenyl)methyl]thio]-4-[(2-hydroxyethyl)amino]-7(8H)-pteridinone (2R)-2-[[2-[[2,3-Difluorophenyl)methyl]thio]-7,8-dihydro-7-oxo-4-pteridinyl]amino]-propanamide 2-[[(3-Chloro-2-fluorophenyl)methyl]thio]-4-[[(1R)-2-hydroxy-1-methylethyl]amino]-7(8H)-pteridinone 2-[[(3-Chloro-2-fluorophenyl)methyl]thio]-4-[(2-hydroxyethyl)amino]-7(8H)-pteridinone 2-[[(3-Chloro-2-fluorophenyl)methyl]thio]-4-[[2-hydroxy-1-(hydroxymethyl)ethyl]amino]-7(8H)-pteridinone

[(2R)-2-[[2-[[(3-Chloro-2-fluorophenyl)methyl]thio]-7,8-dihydro-7-oxo-4-pteridinyl]amino]propyl]-carbamic acid, 1,1-dimethylethyl ester 4-[[(1R)-2-Amino-1-methylethyl]amino]-2-[[(3-chloro-2-fluorophenyl)methyl]thio]-7(8)-pteridinone, monohydrochloride 2-[[(3-Chloro-4-methoxyphenyl)methyl]thio]-4-[[2-hydroxy-1-(hydroxymethyl)ethyl]amino]-7(8H)-pteridinone 4-[(2-Aminoethyl)amino]-2-[[(3-chloro-4-methoxyphenyl)methyl]thio]-7(8H-pteridinone, monotrifluoroacetate 2-[[(2-Fluoro-4-methoxyphenyl)methyl]thio]-4-[[(1R)-2-hydroxy-1-methylethyl]amino]-7(8H)-pteridinone 2-[[(2-Fluoro-3-methylphenyl)methyl]thio]-4-[[(1R)-2-hydroxy-1-methylethyl]amino]-7(8H)-pteridinone 2-[[(3-Fluoro-2-methoxyphenyl)methyl]thio]-4-[[(1R)-2-hydroxy-1-methylethyl]amino]-7(8H)-pteridinone 2-[[[4-(Difluoromethoxy)phenyl]methyl]thio]-4-[[(1R)-2-hydroxy-1-methylethyl]amino]-7(8H)-pteridinone 4-[[(1R)-2-Hydroxy-1-methylethyl]amino]-2-[[(4-hydroxyphenyl)methyl]thio]-7(8H)-pteridinone 4-[[(1R)-2-Hydroxy-1-methylethyl]amino]-2-[[(3-methylphenyl)methyl]thio]-7(8H)-pteridinone 2-[(1,3-Benzodioxol-4-ylmethyl)thio]-4-[[(1R)-2-hydroxy-1-methylethyl]amino]-7(8H)-pteridinone 2-[[(2,4-Difluorophenyl)methyl]thio]-4-[[(1R)-2-hydroxy-1-methylethyl]amino]-7(8H)-pteridinone 2-[[(3-Chlorophenyl)methyl]thio]-4-[[(1R)-2-hydroxy-1-methylethyl]amino]-7(8H)-pteridinone 4-[[(1R)-2-Hydroxy-1-methylethyl]amino]-2-[(5-isoxazolylmethyl)thio]-7(8H)-pteridinone
4-[[-2-Hydroxy-1-(hydroxymethylethyl]amino]-2-[(5-isoxazolylmethyl)thio]-7(8H)-pteridinone
4-[[(1R)-2-Hydroxy-1-methylethyl]amino]-2-[[(5-methyl-2-furanyl)methyl]thio]-7(8H)-pteridinone
2-[[(2-Fluorophenyl)methyl]thio]-4-[[(1R)-2-hydroxy-1-methylethyl]amino]-7(8H)-pteridinone
4-[[(1R)-2-Hydroxy-1-methylethyl]amino]-2-[[(2-thienyl)methyl)thio]-7(8H)-pteridinone
2-[[(2-Fluorophenyl)methyl]thio]-4-[[-2-hydroxy-1-(hydroxymethylethyl]amino]-7(8H)-pteridinone
4-[[-2-Hydroxy-1-(hydroxymethyl)ethyl]amino]-2-[(2-thienylmethyl)thio]-7(8H)-pteridinone
2-[[(2-Fluoro-5-methylphenyl)methyl]thio]-4-[[(1R)-2-hydroxy-1-methylethyl]amino]-7(8H)-pteridinone
2-[[(2-Fluoro-3-(trifluoromethyl)phenyl)methyl]thio]-4-[[(1R)-2-hydroxy-1-methylethyl]amino]-7(8H)-pteridinone
2-[[(2-Fluoro-3-(trifluoromethyl)phenyl)methyl]thio]-4-[[2-hydroxy-1-(hydroxymethyl)ethyl]amino]-7(8H)-pteridinone
2-[[(2-Fluoro-3-(trifluoromethyl)phenyl)methyl]thio]-4-[(2-hydroxyethyl)amino]-7(8H)-pteridinone
4-[(2-aminoethyl)amino]-2-[[(2-fluoro-3-(trifluoromethyl)phenyl)methyl]thio]-7(8H)-pteridinone
2-[[(2,3-Difluorophenyl)methyl]thio]-4-[[2-hydroxy-1-(hydroxymethyl)-1-methylethyl]amino]-7(8H)-pteridinone
2-[[(2,3-Difluorophenyl)methyl]thio]-4-[[(1R)-2-hydroxy-1-methylethyl]amino]-6-methyl-7(8H)-pteridinone
2-[[(2,3-Difluorophenyl)methyl]thio]-7,8-dihydro-4-[[(1R)-2-hydroxy-1-methylethyl]amino]-7-oxo-6-pteridinecarboxylic acid ethyl ester
2-[[(2,3-Difluorophenyl)methyl]thio]-4-[[(1R)-2-hydroxy-1-methylethyl]amino]-6-(trifluoromethyl)-7(8H)-pteridinone
2-[[(2,3-Difluorophenyl)methyl]thio]4-[[(1R)-2-hydroxy-1-methylethyl]amino]-7(8H)-pteridinone sodium salt
2-[(2,3-difluorobenzyl)thio]-4-(ethylamino)-7(8H)-pteridinone
2-[(2,3-difluorobenzyl)thio]-4-(isopropylamino)-7(8H)-pteridinone
(+/−)-4-(sec-butylamino)-2-[(2,3-difluorobenzyl)thio]-7(8H)-pteridinone
2-({2-[(2,3-difluorobenzyl)thio]-7-oxo-7,8-dihydro-4-pteridinyl}amino)acetamide
(+/−)-2-[(2,3-difluorobenzyl)thio]-4-[(2-hydroxypropyl)amino]-7(8H)-pteridinone
(S)-2-[(2,3-difluorobenzyl)thio]-4-[(2-hydroxy-1-methylethyl)amino]-7(8H)-pteridinone
(+/−)-2-[(2,3-difluorobenzyl)thio]-4-[(2-hydroxy-1-methylethyl)amino]-7(8H)-pteridinone
(R)-2-[(2,3-difluorobenzyl)thio]-4-[(2-hydroxypropyl)amino]7(8H)-pteridinone
2-[(2,3-difluorobenzyl)thio]-4-[(3-hydroxypropyl)amino]-7(8H)-pteridinone
2-[(2,3-difluorobenzyl)thio]-4-[(2-hydroxyethyl)(methyl)amino]-7(8H)-pteridinone
3-[{2-[(2,3-difluorobenzyl)thio]-7-oxo-7,8-dihydro-4-pteridinyl}(methyl)amino]propanenitrile
(R)-2-[(2,3-difluorobenzyl)thio]-4-{[1-(hydroxymethyl)propyl]amino}-7(8H)-pteridinone
(R)-2-[(2,3-difluorobenzyl)thio]-4-{[1-(hydroxymethyl)propyl]amino}-7(8H)-pteridinone
2-[(2,3-difluorobenzyl)thio]-4-[(4-hydroxybutyl)amino]-7(8H)-pteridinone
(+/−)-2-[(2,3-difluorobenzyl)thio]-4-{[1-(hydroxymethyl)propyl]amino}-7(8H)-pteridinone
2-[(2,3-difluorobenzyl)thio]-4-[(2-hydroxy-1,1-dimethylethyl)amino]-7(8H)-pteridinone
2-[(2,3-difluorobenzyl)thio]-4-[ethyl(2-hydroxyethyl)amino]-7(8H)-pteridinone
(+/−)-4-[(3-amino-2-hydroxypropyl)amino]-2-[(2,3-difluorobenzyl)thio]-7(8H)-pteridinone
(+/−)-2-[(2,3-difluorobenzyl)thio]-4-[(1,3-dimethylbutyl)amino]-7(8H)-pteridinone
(1R,2R)-2-[(2,3-difluorobenzyl)thio]-4-[(2-hydroxycyclopentyl)amino]-7(8H)-pteridinone
2-[(2,3-difluorobenzyl)thio]-4-[(5-hydroxypentyl)amino]-7(8H)-pteridinone
(+/−)-2-[(2,3-difluorobenzyl)thio]-4-{[1-(hydroxymethyl)butyl]amino}-7(8H)-pteridinone
(+/−)-methyl 2-({2-[(2,3-difluorobenzyl)thio]-7-oxo-7,8-dihydro-4-pteridinyl}amino)propanoate
2-[(2,3-difluorobenzyl)thio]-4-[(3-hydroxy-2,2-dimethylpropyl)amino]-7(8H)-pteridinone(1R,2R)-2-[(2,3-difluorobenzyl)thio]-4-{[2-hydroxy-1-(hydroxymethyl)propyl]amino}-7(8H)-pteridinone
4-[bis(2-hydroxyethyl)amino]-2-[(2,3-difluorobenzyl)thio]-7(8H)-pteridinone
2-[(2,3-difluorobenzyl)thio]-4-{[2-(2-hydroxyethoxy)ethyl]amino}-7(8H)-pteridinone
2-[(2,3-difluorobenzyl)thio]-4-[(2,2-dimethoxyethyl)amino]-7(8H)-pteridinone
4-{[2-(diethylamino)ethyl]amino}-2-[(2,3-difluorobenzyl)thio]-7(8H)-pteridinone
(S)-2-[(2,3-difluorobenzyl)thio]-4-{[1-(hydroxymethyl)-2,2-dimethylpropyl]amino}-7(8H)-pteridinone
(R)-2-[(2,3-difluorobenzyl)thio]-4-{[1-(hydroxymethyl)-3-methylbutyl]amino}-7(8H)-pteridinone
2-[(2,3-difluorobenzyl)thio]-4-[(6-hydroxyhexyl)amino]-7(8H)-pteridinone
2-[(2,3-difluorobenzyl)thio]-4-{[3-(dimethylamino)-2,2-dimethylpropyl]amino}-7(8H)-pteridinone
(S)-ethyl 2-({2-[(2,3-difluorobenzyl)thio]-7-oxo-7,8-dihydro-4-pteridinyl}amino)-3-hydroxypropanoate and pharmaceutically acceptable salts and solvates thereof.

According to the invention there is also provided a process for the preparation of a compound of formula (I) which comprises:

(a) treatment of a compound of formula (IIA):

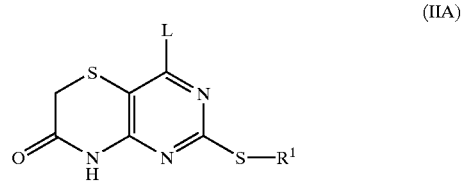

(IIA)

where $R^1$ is as defined in formula (I) or is a protected derivative thereof and L is a leaving group with an amine $HNR^2R^3$, or (b) treatment of a compound of formula (IIB):

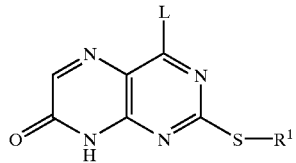

(IIB)

where $R^1$ is as defined in formula (I) or is a protected derivative thereof and L is a leaving group with an amine $HNR^2R^3$, or (c) treatment of a compound of formula (IIC):

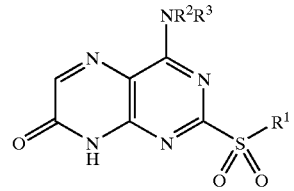

(IIC)

where $R^1$, $R^2$ and $R^3$ are as defined in formula (I) or are protected derivatives thereof with a thiol $R^1SH$, or (d) treatment of a compound of formula (IID):

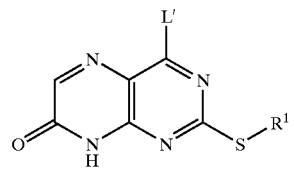

(IID)

where $R^1$ is as defined in formula (I) or is a protected derivative thereof and L' is a leaving group with an amine $HNR^2R^3$, and optionally thereafter process (a), (b), (c) or (d) and in any order:

removing any protecting groups forming a pharmaceutically acceptable salt.

The reaction of compounds of formula (IIA) and (IIB) with an amine $HNR^2R^3$ can be carried out in a solvent such as N-methyl-pyrrolidinone at a temperature between 0° C. and 150° C. Suitable leaving groups L include halogen, especially chloro or bromo.

The reaction of compounds (IIC) with a thiol $R^1SH$ can be carried out in a solvent such as N-methylpyrrolidinone using a base such as potassium tert-butoxide at a temperature between 0° C. and 150° C.

The reaction of compounds of formula (IID) with an amine $HNR^2R^3$ can be carried out using either neat amine $HNR^2R^3$ or in a solvent such as 1-methylimidazole at a temperature between 50° C. and 200° C. with or without the assistance of microwave radiation.

Compounds of formula (IIA) where $R^1$ is as defined in formula (I) and L is a leaving group such as chlorine may be prepared by treatment of a compound of formula (IIA) where $R^1$ is as defined above and L is a hydroxyl group with a halogenating agent such as phosphorus oxychloride. The reaction may be carried out in a at reflux in the presence of N,N-dimethylaniline.

Compounds of formula (IIA) where $R^1$ is as defined in formula (I) and L is a hydroxyl group may be prepared by acid treatment of a compound of formula (III) where $R^1$ and L are as defined above. Suitable acids include p-toluene sulphonic acid and the reaction may be carried out in a solvent such as toluene at reflux.

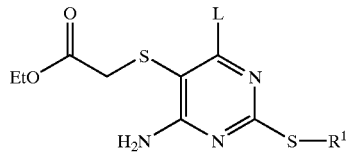

(III)

Compounds of formula (III) where $R^1$ is as defined in formula (I) and L is a hydroxyl group may be prepared by treatment of a compound of formula (IV) where $R^1$ and L are as defined above with a reducing agent in the presence of ethyl bromoacetate. The reaction may be carried out in a solvent such as ethanol at room temperature using a reducing agent such as sodium borohydride.

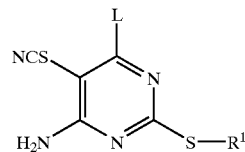

(IV)

Compounds of formula (IV) where $R^1$ is as defined in formula (I) and L is a hydroxyl group may be prepared by treatment of a compound of formula (V) where $R^1$ and L are as defined above with a metal thiocyanate in the presence of bromine. The reaction may be performed in a solvent such as N,N-dimethylformamide at a temperature between 0° C. and 100° C. in the presence of pyridine using potassium thiocyanate.

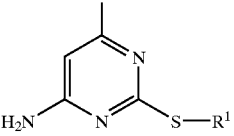

(V)

Compounds of formula (V) where $R^1$ is as defined in formula (I) and L is a hydroxyl group are suitably prepared by reacting a compound of formula (VI):

(VI)

with a compound of formula $R^1X$ where $R^1$ is as defined above and X is a leaving group such as bromide in the presence of a base such as sodium hydroxide. The reaction may be carried out in aqueous NMP at room temperature.

Compounds of formula (VI) are commercially available.

Compounds of formula (IIB) where $R^1$ is as defined in formula (I) and L is a leaving group such as bromo may be prepared by treating a compound of formula (IIB) where $R^1$ is as defined above and L is $NH_2$ with a diazotizing agent such as isoamyl nitrite in the presence of a halogenating agent such as bromoform. The reaction may be performed in a solvent such as DMSO at a temperature between 0° C. and 100° C.

Compounds of formula (IIB) where $R^1$ is as defined in formula (I) and L is $NH_2$ may be prepared by either:
i) Treatment of a compound of formula (VII):

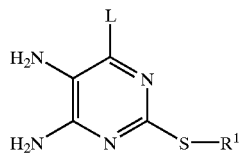

(VII)

where $R^1$ and L are as defined above with ethyl glyoxylate in the presence of a base such as sodium methoxide in a solvent such as methanol at room temperature, or
ii) Treatment of a compound of formula (VIII):

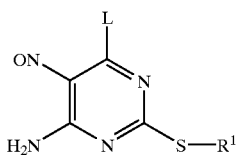

(VIII)

where $R^1$ and L are as defined above with triethyl phosphonoacetate in the presence of a base such as butyllithium. The reaction may be carried out in a solvent such as DMF at a temperature between 0° C. and 100° C.

Compounds of formula (VII) where $R^1$ is as defined in formula (I) and L is $NH_2$ may be prepared by treating a compound of formula (VIII) where $R^1$ and L are as defined above with a reducing agent such as sodium hydrosulphite. The reaction may be carried out in a solvent such as water at reflux.

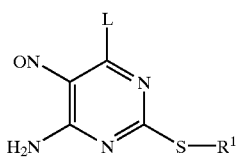

(VIII)

Compounds of formula (VIII) where $R^1$ is as defined in formula (I) and L is $NH_2$ may be prepared by treating a compound of formula (IX) where $R^1$ and L are as defined above with a nitrosating agent such as sodium nitrite. The reaction may be performed in a solvent such as aqueous acetic acid at a temperature between 0° C. and 100° C.

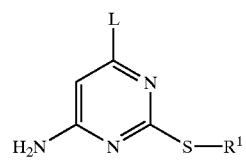

(IX)

Compounds of formula (IX) where $R^1$ is as defined in formula (I) and L is $NH_2$ may be prepared by treating a compound of formula (X) with a compound of formula $R^1X$ where $R^1$ is as defined above and X is a leaving group such as bromide in the presence of a base such as potassium tert-butoxide. The reaction may be performed in a solvent such as DMSO at room temperature.

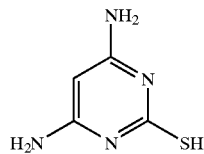

(X)

Compounds of formula (IIC) where $R^1$, $R^2$ and $R^3$ are as defined in formula (I) may be prepared from compounds of formula (I) where $R^1$, $R^2$ and $R^3$ are as defined in formula (I) by treatment with a peracid such as peracetic acid. The reaction may be performed in a solvent such as acetic acid at a temperature between 0° C. and 100° C.

Compounds of formula (IID) where $R^1$ is as defined in formula (I) and L is an alkoxy group may be prepared from compounds of formula (IID) where $R^1$ is as defined in formula (I) and L is a thioalkyl group by treatment with a suitable alcohol in the presence of a base, Suitable alcohols include isopropanol and the base may be sodium and the reaction may be performed at a temperature between 0° C. and 150° C.

Compounds of formula (IID) where $R^1$ is as defined in formula (I) and L is a thioalkyl group may be prepared from compounds of formula (XI) by sequential treatment with an alkyl halide $R^1X$ followed by ethyl glyoxalate in the presence of a base. The reaction may be performed in a solvent such as methanol at a temperature between 0° C. and 150° C. using sodium as the base.

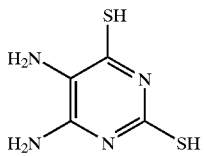

(XI)

Compounds of formula (X) and (XI) are commercially available.

It will be appreciated by those skilled in the art that in the processes of the present invention certain functional groups such as hydroxyl or amino groups in the starting reagents or intermediate compounds may need to be protected by protecting groups. Thus, the preparation of the compounds of formula (I) may involve, at an appropriate stage, the removal of one or more protecting groups. The protection and deprotection of functional groups is fully described in 'Protective Groups in Organic Chemistry', edited by J. W. F. McOmie, Plenum Press (1973), and 'Protective Groups in Organic Synthesis', 2nd edition, T. W. Greene & P. G. M. Wuts, Wiley-Interscience (1991).

Novel intermediate compounds form a further aspect of the invention. In particular compounds of formula (IIA) and (IIB) are novel and form an aspect of the invention.

The compounds of formula (I) above may be converted to a pharmaceutically acceptable salt or solvate thereof, preferably a basic addition salt such as sodium, potassium, calcium, aluminium, lithium, magnesium, zinc, benzathine, chloroprocaine, choline, diethanolamine, ethanolamine, ethyldiamine, meglumine, tromethamine or procaine, or an acid addition salt such as a hydrochloride, hydrobromide, phosphate, acetate, fumarate, maleate, tartrate, citrate, oxalate, methanesulphonate or p-toluenesulphonate.

The compounds of formula (I) have activity as pharmaceuticals, in particular as modulators of chemokine receptor (especially CXCR2) activity, and may be used in the treatment (therapeutic or prophylactic) of conditions/diseases in human and non-human animals which are exacerbated or caused by excessive or unregulated production of chemokines. Examples of such conditions/diseases include:

(1) (the respiratory tract) obstructive airways diseases including chronic obstructive pulmonary disease (COPD); asthma, such as bronchial, allergic, intrinsic, extrinsic and dust asthma, particularly chronic or inveterate asthma (e.g. late asthma and airways byperresponsiveness); bronchitis; acute, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia;

(2) (bone and joints) rheumatoid arthritis, seronegative spondyloarthropathies (including ankylosing spondylitis, psoriatic arthritis and Reiter's disease), Beheet's disease, Sjogren's syndrome and systemic sclerosis;

(3) (skin) psoriasis, atopical dermatitis, contact dermatitis and other eczmatous dermitides, seborrhoetic dermatitis, Lichen planus, Pemphigus, bullous Pemphigus, Epidermolysis bullosa, urticaria, angiodermas, vasculitides, erythemas, cutaneous eosinophilias, uveitis, Alopecia areata and vernal conjunctivitis;

(4) (gastrointestinal tract) Coeliac disease, proctitis, eosinopilic gastro-enteritis, mastocytosis, Crohn's disease, ulcerative colitis, food-related allergies which have effects remote from the gut, e.g., migraine, rhinitis and eczema;

(5) (central and peripheral nervous system) Neurodegenerative diseases and dementia disorders, e.g. Alzheimer's disease, amyotrophic lateral sclerosis and other motor neuron diseases, Creutzfeldt-Jacob's disease and other prior diseases, HIV encephalopathy (AIDS dementia complex), Huntington's disease, frontotemporal dementia, Lewy body dementia and vascular dementia; polyneuropathies, e.g. Guillain-Barré syndrome, chronic inflammatory demyelinating polyradiculoneuropathy, multifocal motor neuropathy, plexopathies; CNS demyelination, e.g. multiple sclerosis, acute disseminated/haemorrhagic encephalomyelitis, and subacute sclerosing panencephalitis; neuromuscular disorders, e.g. myasthenia gravis and Lambert-Eaton syndrome; spinal disorders, e.g. tropical spastic paraparesis, and stiff-man syndrome: paraneoplastic syndromes, e.g. cerebellar degeneration and encephalomyelitis; CNS trauma; migraine; and stroke.

(6) (other tissues and systemic disease) atherosclerosis, Acquired Immunodeficiency Syndrome (AIDS), lupus erythematosus, systemic lupus, erythematosus, Hashimoto's thyroiditis, type I diabetes, nephrotic syndrome, eosinophilia fascitis, hyper IgE syndrome, lepromatous leprosy, and idiopathic thrombocytopenia pupura; post-operative adhesions, and sepsis.

(7) (allograft rejection) acute and chronic following, for example, transplantation of kidney, heart, liver, lung, bone marrow, skin and cornea; and chronic graft versus host disease;

(8) Cancers, especially non-small cell lung cancer (NSCLC), malignant melanoma, prostate cancer and squamous sarcoma, and tumour metastasis;

(9) Diseases in which angiogenesis is associated with raised CXCR2 chemokine levels (e.g. NSCLC, diabetic retinopathy).

(10) Cystic fibrosis, re-perfusion injury in the heart, brain, peripheral limbs and other organs.

(11) Burn wounds & chronic skin ulcers

(12) Reproductive Diseases (e.g. Disorders of ovulation, menstruation and implantation, Pre-term labour, Endometriosis)

Thus, the present invention provides a compound of formula (I), or a pharmaceutically-acceptable salt or solvate thereof, as hereinbefore defined for use in therapy.

Preferably the compounds of the invention are used to treat diseases in which the chemokine receptor belongs to the CXC chemokine receptor subfamily, more preferably the target chemokine receptor is the CXCR2 receptor, Particular conditions which can be treated with the compounds of the invention are psoriasis, diseases in which angiogenesis is associated with raised CXCR2 chemokine levels, and COPD. It is preferred that the compounds of the invention are used to treat psoriasis.

As a further aspect of the present invention, certain compounds of formula (I) may have utility as antagonists of the CX3CR1 receptor. Such compounds are expected to be particularly useful in the treatment of disorders within the central and peripheral nervous system and other conditions characterized by an activation of microglia and/or infiltration of leukocytes (e.g. stroke/ischemia and head trauma).

In a further aspect, the present invention provides the use of a compound of formula (I), or a pharmaceutically acceptable salt or solvate thereof, as hereinbefore defined in the manufacture of a medicament for use in therapy.

In a still further aspect, the present invention provides the use of a compound of formula (I), or a pharmaceutically acceptable salt or solvate thereof, as hereinbefore defined in the manufacture of a medicament for the treatment of human diseases or conditions in which modulation of chemokine receptor activity is beneficial.

In the context of the present specification, the term "therapy" also includes "prophylaxis" unless there are specific indications to the contrary. The terms "therapeutic" and "therapeutically" should be construed accordingly.

The invention still further provides a method of treating a chemokine mediated disease wherein the chemokine binds to a chemokine (especially CXCR2) receptor, which comprises administering to a patient a therapeutically effective amount of a compound of formula (I), or a pharmaceutically acceptable salt or solvate thereof, as hereinbefore defined.

The invention also provides a method of treating an inflammatory disease, especially psoriasis, in a patient suffering from, or at risk of, said disease, which comprises administering to the patient a therapeutically effective amount of a compound of formula (I), or a pharmaceutically acceptable salt or solvate thereof, as hereinbefore defined.

For the above-mentioned therapeutic uses the dosage administered will, of course, vary with the compound employed, the mode of administration, the treatment desired and the disorder indicated.

The compounds of formula (I) and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (per cent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), or a pharmaceutically acceptable salt or solvate thereof, as hereinbefore defined, in association with a pharmaceutically acceptable adjuvant, diluent or carrier.

The invention further provides a process for the preparation of a pharmaceutical composition of the invention which comprises mixing a compound of formula (I), or a pharmaceutically acceptable salt or solvate thereof, as hereinbefore defined, with a pharmaceutically acceptable adjuvant, diluent or carrier.

The pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally. Preferably the compounds of the invention are administered orally.

The invention will now be further illustrated by reference to the following examples. In the examples the Nuclear Magnetic Resonance (NMR) spectra were measured on a Varian Unity Inova 300 or 400 MHz spectrometer and the Mass Spectrometry (MS) spectra measured on a Finnigan Mat SSQ7000 or Micromass Platform spectrometer. Where necessary, the reactions were performed under an inert atmosphere of either nitrogen or argon. Chromatography was generally performed using Matrex Silica 60® (35–70 micron) or Prolabo Silica gel 60® (35–70 micron) suitable for flash silica gel chromatography. High pressure liquid chromatography purification was performed using either a Waters Micromass LCZ with a Waters 600 pump controller, Waters 2487 detector and Gilson FC024 fraction collector or a Waters Delta Prep 4000. The abbreviations m.p. and DMSO used in the examples stand for melting point and dimethyl sulphoxide respectively.

EXAMPLE 1

4-[[((1R)-2-Hydroxy-1-methylethyl]amino]-2-[(phenylmethyl)thio]-6H-pyrimido[5,4-b][1,4]thiazin-7(8H)-one (a) 6-Amino-1,4-dihydro-2-[(phenylmethyl)thio]-4-oxo-5-thiocyanic acid, pyrimidinyl ester 6-Amino-2-[(phenylmethyl)thio]-4(1H)-pyrimidinone (10.5 g)[preparation as described in WO 9635678] and potassium thiocyanate (25 g) in N,N-dimethylformamide (200 ml) were heated together at 65° C. Pyridine (6.3 ml) was added and the solution cooled to 5° C. Bromine (2.2 ml) was added slowly and the reaction mixture stirred for 2 hours at 5–10° C. The reaction mixture was poured onto ice water, stirred for 1 hour and the solid was isolated by filtration. After washing with water and ether, a pure sample was obtained after trituration with hot methanol.

MS (APCI) 291 (M+H, 100%).

(b) [[6-amino-1,4-dihydro-4-oxo-2-[(phenylmethyl)thio]-5-pyrimidinyl]thio]-acetic acid, ethyl ester To a suspension of the product from step a) (1.5 g) in dry ethanol (100 ml) was added sodium borohydride (0.570 g) and the resultant solution allowed to stir for 15 mins. To this solution was added ethyl bromoacetate (0.570 ml). The mixture was neutralised with concentrated hydrochloric acid then evaporated to dryness and purified ($SiO_2$, ethyl acetate:dichloromethane 1:1 as eluant) to give the subtitle compound as a colourless solid (1.1 g).

MS (APCI) 352 (M+H, 100%).

(c) 2-[(Phenylmethyl)thio]-1H-pyrimido[5,4-b][1,4]thiazine-4,7(6H,8H)-dione

To a solution of the product from step b) (0.30 g) in dry toluene (60 ml) was added p-toluene sulphonic acid (50 mg) and the solution heated under reflux for 11 hours. The resultant solid was collected by filtration, washed with ether and dried to give the subtitle compound as a colourless solid (0.290 g)

MS (APCI) 306 (M+H, 100%).

(d) 4-Chloro-2-[(phenylmethyl)thio]-6H-pyrimido[5,4-b][1,4]thiazin-7(8H)-one

A suspension of the product from step c) (1.5 g), phosphorus oxychloride (10 ml) and N,N-dimethyl aniline (1 ml) was heated under reflux for 2 hours. The mixture was allowed to cool to room temperature and poured carefully into a saturated sodium bicarbonate solution, and stirred for 15 mins. The crude product was extracted into ethyl acetate and purified ($SiO_2$, dichloromethane as eluant) to give the subtitle compound (0.25 g)

MS (APCI) 324 (M+H$^+$, 100%).

(e) 4-[[(1R)-2-Hydroxy-1-methylethyl]amino]-2-[(phenylmethyl)thio]-6H-pyrimido[5,4-b][1,4]thiazin-7(8H)-one The product from step e) (0.250 g) in NMP (5 ml) was treated with (R)-2-amino-1-propanol (0.116 g) and the reaction mixture was heated at 110° C. for 2 hours. The mixture was evaporated to dryness and the residue purified (HPLC, Symmetry® C18 column, 0.1% aqueous ammonium acetate:acetonitrile isocratic elution 75:25) to afford the title compound (0.13 g).

MS: APCI 363 (M+H)

$^1$H NMR: δ (DMSO) 10.84 (1H, s), 7.47–7.19 (5H, m), 6.26 (1H, d), 4.78 (1H, t), 4.36–4.19 (3H, m), 3.55–3.32 (4H, m), 1.12 (3H, d).

EXAMPLE 2

2-[[(2,3-Difluorophenyl)methyl]thio]-4-[[(1R)-2-hydroxy-1-methylethyl]amino]-7(8H)-pteridinone a) 2-[[(2,3-Difluorophenyl)methyl]thio]-4,6-pyrimidinediamine 4,6-diamino-2-pyrimidinethiol (7.3 g) was dissolved in DMSO (100 ml) at room temperature under an atmosphere of nitrogen. Potassium tert-butoxide (1M in THF, 48.3 ml) was added followed by 2,3-difluorobenzyl-bromide (10.0 g). The mixture was stirred for 2 hours at room temperature. The reaction mixture was then partitioned between ethyl acetate and ammonium chloride. The organic phase was washed with ammonium chloride (3×) and brine, then dried over magnesium sulphate and evaporated to give the subtitled product as a white solid (12.2 g)

MS: ADCI (+ve) 269 (M+1)

b) 2-[[(2,3-Difluorophenyl)methyl]thio]-5-nitroso-4,6-pyrimidinediamine

The product of step (a) (2.5 g) was dissolved in acetic acid (150 ml) and the solution cooled to 5° C. A solution of sodium nitrite (625 mg) in water (50 ml) was added dropwise resulting in a dark blue colouration. The reaction was stirred at room temperature for 30 minutes during which time a pink solid precipitated from solution. This was isolated by filtration and washed with water, then dried at 50° C. to give the sub-titled product as a blue solid (4.14 g)

MS: ADCI (+ve) 298 (M+1)

¹H NMR: δ (DMSO) 4.44 (s,2H), 7.13–7.54 (m,3H), 8.13 (s,1H), 8.51 (s,1H), 9.10 (s,1H), 10.18 (s,1H).

c) 2-[[(2,3-Difluorophenyl)methyl]thio]-4,5,6-pyrimidinetriamine

To a suspension of the product of step (b) (2 g) in boiling water (40 ml) was added $Na_2S_2O_4$ (5.4 g) portion-wise. The suspension was allowed to cool and then 50% sulphuric acid was added slowly and then the mixture was cooled to 0° C. The solid was isolated by filtration and washed with cold water, then dried over $P_2O_5$ at 50° C. to give the sub-titled product as a yellow solid.

MS: ADCI (+ve) 284 (M+1)

¹H NMR: δ (DMSO) 4.33 (s,2H), 6.42 (brs,3H), 7.10–7.48 (m,3H)

d) 4-amino-2-[[(2,3-difluorophenyl)methyl]thio]-7(8H)-pteridinone

The product of step (c) (100 mg) was dissolved in a solution of sodium (0.05 g) in methanol (5 ml). This was left to stir for 15 min at room temperature, then ethyl glyoxalate (134 μl) was added to the mixture which was left to stir for 12 hr at room temperature. Water (5 ml) was added, then concentrated hydrochloric acid was slowly added to acidify the solution to ~pH5 whereupon a solid precipitated which was isolated by filtration and dried over $P_2O_5$ at 50° C. to yield a pale yellow solid (44.5 mg).

MS: ADCI (+ve) 322 (M+1)

¹H NMR: δ (DMSO) 4.18 (s,2H), 7.11–7.58 (m,3H), 7.84 (s,1H), 12.69 (bs,1H)

e) 4-bromo-2-[[(2,3-difluorophenyl)methyl]thio]-7(8H)-pteridinone

The product of step (d) (6.0 g) was suspended in DMSO (90 ml) and bromoform (60 ml) was added and the mixture was heated to 100° C. Isopentylnitrite (25 ml) was added and the mixture stirred for 5 min. The mixture was quickly cooled in an ice bath then evaporated to leave an oil. This was repeated three times. Acetonitrile (200 ml) was added and the solid which separated was removed by filtration. The solvent was evaporated and the residue was purified by flash chromatography, eluting with dichloromethane and then 5% ethyl acetate in dichloromethane to give a yellow solid which was slurried with ether then collected. The solid was washed with ether and dried to give the subtitled compound as a colourless solid (8.74 g).

MS: APCI (–ve) 382/4 (M–H), 382 (100%)

¹H NMR: δ (DMSO) 4.47 (s, 2H), 7.13–7.55 (m,3H), 8.14 (s,1H), 13.33 (bs,1H)

f) 2-[[(2,3-difluorophenyl)methyl]thio]-4-[[(1R)-2-hydroxy-1-methylethyl]amino]-7(8H)-pteridinone The product of step (e) (8.7 g) was dissolved in N-methylpyrrolidinone (40 ml) and Hunigs base (7.9 ml) was added followed by D-alaninol (2.7 ml). The mixture was stirred at 100° C. for 15 mins. The cooled solution was poured onto water, (1l), and acidified with dilute hydrochloric acid. The solid which separated was collected, washed with water and air dried. Crystallisation from acetonitrile afforded the title compound as a pale yellow solid (7.4 g).

m.p. 215–217° C.

MS: APCI (+ve) 380 (M+H, 100%)

¹H NMR: δ (DMSO) 1.14 (d, 3H), 3.48 (m, 2H), 4.31 (m, 1H), 4.45 (dd, 2H) 4.82 (t, 1H) 7.15 (m, 1H), 7.33 (m, 1H), 7.47 (t, 1H), 7.76 (d, 1H), 7.83 (d,1H), 12.70 (s, 1H).

Alternatively, example 2 may be prepared by the following procedure:

g) 2,4-bis[[(2,3-difluorophenyl)methyl]thio]-7(8H)-pteridinone

Sodium (3.96 g) was dissolved in methanol (150 ml), 5,6-diamino-2,4-pyrimidinedithiol (15 g) was added, then 2,3-difluorobenzylbromide (30.9 g) slowly added and the reaction mixture was stirred at room temperature under nitrogen for 10 min. Ethyl glyoxalate (15 ml) was added followed by more sodium (2.5 g) and the reaction was left for a further 20 min. The reaction was then quenched with acetic acid (10 ml) and poured on to water (600 ml) with stirring. The resulting precipitate was filtered through celite and washed with water. The filtrate was discarded and the solid was washed through the celite using acetone. The solution was then evaporated to dryness and purified by silica gel column chromatography using 10% ethyl acetate in DCM to yield the sub-titled compound as a cream solid (8 g).

MS: APCI (+ve) 465 (M+1)

h) 2-[[(2,3-Difluorophenyl)methyl]thio]-4-[[(1R)-2-hydroxy-1-methylethyl]amino]-7(8H)-pteridinone The product of example 2, step (g) (2.3 g) and D-alaninol (5 g) were microwaved at 150° C. for 5 min. The resulting solution was partitioned between ethyl acetate and aqueous ammonium chloride and the organic layer was washed with ammonium chloride (2×50 ml). The organic layer was evaporated to dryness and purified twice by silica gel chromatography using first 20:1 DCM:methanol and then 1:1 DCM:ethyl acetate to yield the titled compound (220 mg).

MS: APCI (+ve) 380 (M+1)

EXAMPLE 3

2-[[(2,3-Difluorophenyl)methyl]thio]-4-[[2-hydroxy-1-(hydroxymethyl)ethyl]amino]-7(8H)-pteridinone a) 4-amino-2-[[(2,3-difluorophenyl)methyl]thio]-7(8H)-pteridinone To a solution of triethyl phosphonoacetate (15.0 g) in tetrahydrofuran (60 ml) cooled in an ice bath was added butyllithium (2.5 M in hexanes, 25.6 ml) at a rate such that the internal temperature was maintained below 30° C. To this mixture was then added a solution of the product of Example 2 step (b) (10.0 g) in N,N-dimethylformamide (60 ml). The reaction mixture was heated at reflux for 1 hour, then cooled to room temperature and quenched with acetic acid (6 ml). The solid thus precipitated was isolated by filtration, washed with water, ethanol and diethyl ether, and dried over $P_2O_5$ at 50° C. to give the sub-titled product as a pale green solid (9.3 g).

MS: ADCI (+ve) 322 (M+1)

¹H NMR: δ (DMSO) 4.18 (s,2H), 7.11–7.58 (m,3H), 7.84 (s,1H), 12.69 (bs,1H)

b) 4-bromo-2-[[(2,3-difluorophenyl)methyl]thio]-7(8H)-pteridinone

The product of step (a) (0.5 g) was suspended in DMSO (10 ml) and bromoform (10 ml) and the mixture was heated to 125° C. Isoamylnitrite (2 ml) was added and the mixture was stirred at 125° C. for 5 minutes before being cooled in an ice bath. Solvent was removed by evaporation under high vacuum and the residue suspended in dichloromethane (100 ml). This suspension was washed with saturated aqueous ammonium chloride (50 ml) and then filtered through a plug of celite. The filtrate was evaporated and purified by column chromatography, eluting with 10% ethyl acetate in dichloromethane to give the subtitled compound as a white solid (0.22 g).

MS: ADCI (+ve) 386 (M+1)

¹H NMR: δ (DMSO) 4.47 (s,2H), 7.13–7.55 (m,3H), 8.14 (s,1H), 13.33 (bs,1H)

c) 2-[[(2,3-Difluorophenyl)methyl]thio]-4-[[2-hydroxy-1-(hydroxymethyl)ethyl]amino]-7(8H)-pteridinone The titled compound (57 mg) was prepared from the product of step (b) (80 mg) and 2-amino-1,3-propanediol (29 mg) using the method of Example 2 step (f).

MS: ADCI (+ve) 396 (M+1)

$^1$H NMR: δ (DMSO) 12.73 (1H, br s), 7.85 (1H, s), 7.50 (2H, m), 7.33 (1H, m), 7.15 (1H, m), 4.80 (2H, t), 4.45 (2H, s), 4.23 (1H, m), 3.55 (4H, m).

EXAMPLE 4

2-[[(2,3-Difluorophenyl)methyl]thio]-4-[(2-hydroxyethyl)amino]-7(8H)-pteridinone The titled compound (52 mg) was prepared from the product of Example 3 step (b) (150 mg) and ethanolamine (35 ul) using the method of Example 2 step (f).

MS: ADCI (+ve) 366 (M+1)

$^1$H NMR: δ (DMSO) 12.71 (1H, br s), 8.09 (1H, br t), 7.84 (1H, s), 7.47 (1H, m), 7.32 (1H, m), 7.16 (1H, m), 4.78 (1H, t), 4.45 (2H, s), 3.53 (4H, m).

EXAMPLE 5

(2R)-2-[[2-[[2,3-Difluorophenyl)methyl]thio]-7,8-dihydro-7-oxo-4-pteridinyl]amino]-propanamide The titled compound (160 mg) was prepared from the product of Example 3 step (b) (500 mg) and D-alanine amide hydrochloride (172 mg) using the method of Example 2 step (f).

MS: ADCI (+ve) 393 (M+1)

$^1$H NMR: δ (DMSO) 12.77 (1H, br s), 7.88 (1H, s), 7.85 (1H, d), 7.55 (1H, br s), 7.47 (1H,t), 7.36 (1H, m), 7.19 (1H, br s), 7.16 (1H, m), 4.60 (1H, q), 4.46 (2H, q), 1.40 (3H, d).

EXAMPLE 6

2-[[(3-Chloro-2-fluorophenyl)methyl]thio]-4-[[(1R)-2-hydroxy-1-methylethyl]amino]-7(8H)-pteridinone a) 4-Amino-2-[(phenylmethyl)thio]-7(8H)-pteridinone The subtitled compound (16.5 g) was prepared by the method of Example 3, step (a) using 5-nitroso-2-[(phenylmethyl)thio]-4,6-pyrimidinediamine (22.5 g).

MS (ESI) 286 (M+H, 100%).

b) 4-Amino-2-[(phenylmethyl)sulfonyl]-7(8H)-pteridinone

A suspension of the product from example 6, step (a) (5.00 g) in acetic acid (500 ml) and peracetic acid (36–40 wt. % solution in acetic acid, 50 ml) was stirred at 50° for 1 hour. After quenching with dimethylsulphide (15 ml) the solution was poured into ice-water (5000 ml). The suspended solid was removed by filtration and dried in-vacuo to give the subtitled compound as a pale yellow powder (4.53 g).

MS (ESI) 316 (M–H, 100%).

c) 3-Chloro-2-fluoro-benzenemethanethiol

3-Chloro-2-fluorobenzyl bromide (1.00 g) and thiourea (0.35 g) were heated together at reflux in ethanol (10 ml) for 1 hour. The solvent was removed in-vacuo and the residue was suspended in 10% aqueous sodium hydroxide (10 ml) and heated at reflux for 3 hours. The solution was then acidified with conc. HCl and extracted into ether. Concentration of the organic phase in-vacuo gave the subtitle compound as a pale yellow oil (0.71 g).

MS (EI) 176/178 (M+), 143/145 (100%).

d) 4-Amino-2-[[(3-chloro-2-fluorophenyl)methyl]thio]-7(8H)-pteridinone

The product from example 6, step (c) (0.63 g) and 1M t-butoxide solution in THF (3.5 ml) were added to a suspension of the product from example 6, step (b) (1.11 g) in NMP (20 ml). The mixture was stirred vigorously for 1 hour, poured into 1M HCl (15 ml) and diluted with water. The suspended solid was removed by filtration and dried in-vacuo to give the subtitled compound as a pale yellow powder (1.14 g).

MS (ESI) 338 (M+H, 100%).

e) 4-Bromo-2-[[(3-chloro-2-fluorophenyl)methyl]thio]-7(8H)-pteridinone

The subtitled compound (0.318 g) was prepared by the method of Example 3, step (b) using the product from example 6, step (d) (1.10 g).

MS (ESI) 399/401 (M–H, 100%).

f) 2-[[(3-Chloro-2-fluorophenyl)methyl]thio]-4-[[(1R)-2-hydroxy-1-methylethyl]amino]-7(8,H)-pteridinone The titled compound was prepared by the method of Example 2, step (f) using the product from example 6, step (e) (75 mg). The reaction mixture was poured into water and acidified with conc. HCl. The suspended solid was removed by filtration, dried in air and recrystallized from acetonitrile to give a yellow solid (37 mg).

m.p. 209–211°

MS (APCI) 396 (M+H, 100%).

$^1$H NMR: δ (DMSO) 12.71 (1H, br s), 7.83 (1H, s), 7.76 (1H, d), 7.64 (1H, t), 7.48 (1H, t), 7.17 (1H, t), 4.82 (1H, t), 4.39–4.48 (2H, m), 4.28 (1H, m), 3.40–3.52 (2H, m), 1.13 (3H, d).

EXAMPLE 7

2-[[(3-Chloro-2-fluorophenyl)methyl]thio]-4-[(2-hydroxyethyl)amino]-7(8H)-pteridinone The titled compound (51 mg) was prepared by the method of Example 6, step (f) using the product from Example 6, step (e) (75 mg) and ethanolamine (25 μl).

m.p. 195–196.50°

MS (APCI) 382 (M+H, 100%).

$^1$H NMR: δ (DMSO) 12.71 (1H, br s), 8.08 (1H, br m), 7.84 (1H, s), 7.64 (1H, t), 7.49 (1H, t), 7.17 (1H, t), 4.79 (1H, br m), 4.44 (2H, s), 3.53 (4H,br m).

EXAMPLE 8

2-[[(3-Chloro-2-fluorophenyl)methyl]thio]-4-[[2-hydroxy-1-(hydroxymethyl)ethyl]amino]-7(8H)-pteridinone The titled compound (51 mg) was prepared by the method of Example 6, step (f) using the product from Example 6, step (e) (75 mg) and 2-amino-1,3-propanediol (37 mg).

m.p. 218.5–220.5°

MS (APCI) 412 (M+H, 100%).

$^1$H NMR: δ (DMSO) 12.74 (1H, br s), 7.85 (1H, s), 7.67 (1H, t), 7.50 (2H, m), 7.16 (1H, t), 4.81 (2H, t), 4.44 (2H, s), 4.24 (1H, m), 3.51–3.62 (4H, m).

EXAMPLE 9

[(2R)-2-[[2-[[3-Chloro-2-fluorophenyl)methyl]thio]-7,8-dihydro-7-oxo-4-pteridinyl]amino]propyl]-carbamic acid, 1,1-dimethylethyl ester (a) [(1R)-2-amino-1-methyl-2-oxoethyl]carbamic acid, 9H-fluoren-9-ylmethyl ester A solution of D-Alaninamide hydrochloride (3 g) in 10% sodium carbonate solution (50 ml) and dioxan (50 ml) was treated with FMOC chloride (6.24 g) in dioxane (40 ml) and allowed to stir overnight. The mixture was diluted with water (500 ml) and the product collected by filtration and dried in vacuo to give 9.0 g of the subtitle compound.

MS (ESI) BP 311 (+H)

(b) [(1R)-2-amino-1-methylethyl]carbamic acid, 9H-fluoren-9-ylmethyl ester

To a solution of the product from example 9, step (a) (6.9 g) in THF (100 ml) was added borane-methylsulfide complex (4.4 ml) and the mixture heated under reflux for 2 hours. The mixture was carefully quenched by the addition of methanol (100 ml), evaporated to dryness and the residue taken up into methanol (100 ml) and acidified to pH 1–2 with concentrated hydrochloric acid. Heated under reflux for 30 mins then evaporated to dryness. The residue was triturated with ether to give a solid, which was collected by filtration, dissolved in water and the free base precipitated by the addition of aqueous sodium bicarbonate solution to give the subtitle compound (3.1 g).

MS (ESI) BP 297 (+H)

(c) (2R)-[2-(9H-Fluoren-9-ylmethoxycarbonylamino)-propyl]carbamic acid, 1,1-dimethylethylester To a stirred solution of the product from example 9, step (b) (3.0g) in THF (100 ml) was added ditert-butyldicarbonate (2.2 g) and the mixture stirred at room temp for 30 mins. The mixture was evaporated to dryness and the crude product purified ($SiO_2$, dichloromethane as eluant) to give the subtitle compound (3.8 g).

NMR δH ($CDCl_3$) 7.76 (2H, m), 7.42 (2H, m), 7.39–26 (4H, s), 5.01 (1H, s), 4.85 (1H, s), 4.38 (2H, d), 4.19 (1H, t), 3.77 (1H, m), 3.18 (2H, m), 1.27 (9H, s).

(d) [(2R)-2-aminopropyl]carbamic acid, 1,1-dimethylethyl ester

To a solution of the product from example 9, step (c) (3.8 g) in THF (100 ml) was added piperidine (5 ml) and the mixture allowed to stand for 1 hour at room temp. The mixture was evaporated to dryness and the residue purified ($SiO_2$, 5% methanol:dichloromethane as eluant) to give the subtitle compound as a colourless oil (1.7 g).

NMR δH ($CDCl_3$) 4.95 (1H, s), 3.13 (1H, m), 2.99 (1H, m), 2.87 (1H, m), 1.38 (9H, s), 1.08 (3H, d).

(e) [(2R)-2-[[2-[[(3-Chloro-2-fluorophenyl)methyl]thio]-7,8-dihydro-7-oxo-4-pteridinyl]amino]propyl]-carbamic acid, 1,1-dimethylethyl ester The titled compound (83 mg) was prepared by the method of Example 6, step (f) using the product from Example 6, step (e) (75 mg) and the product from example 9, step (d) (72 mg).

MS (APCI) 495 (M+H, 100%).

$^1$H NMR: δ (DMSO) 7.95 (1H, br d), 7.83 (1H, s), 7.62 (1H, t), 7.48 (1H, t), 7.17 (1H, t), 6.94 (1H, br t), 4.34–4.53 (3H, m), 3.04–3.17 (2H, m), 1.32 (9H, s), 1.11 (3H, d).

EXAMPLE 10

4-[[(1R)-2-Amino-1-methylethyl]amino]-2-[[(3-chloro-2-fluorophenyl)methyl]thio]-7(8H)-pteridinone, monohydrochloride A two-phase mixture of the product from Example 9 (76 mg) in 1,4-dioxane (3 ml) and conc. HCl (0.3 ml) was stirred for 2 hours, then diluted with water (10 ml) and lyophilised. The residue was dissolved in water (10 ml), washed with ethyl acetate (5 ml), and lyophilised to give the titled compound as a pale yellow solid (58 mg).

MS (APCI) 395 (M+H parent amine, 100%).

$^1$H NMR: δ ($D_2O$) 7.86 (1H, s), 7.35 (1H, br t), 7.18 (1H, br t), 6.95 (1H, br t), 4.62 (1H, m), 4.20–4.41 (2H, m), 3.14–3.29 (2H, m), 1.33 (3H, br d).

EXAMPLE 11

2-[[(3-Chloro-4-methoxyphenyl)methyl]thio]-4-[[2-hydroxy-1-(hydroxymethyl)ethyl]amino]-7(8H)-pteridinone a) 4-Amino-2-[[(3-chloro-4-methoxyphenyl)methyl]thio]-7(8H)-pteridinone The subtitled compound (1.36 g) was prepared by the method of Example 6, step (d) using the product from Example 6, step (b) (1.21 g) and 3-chloro-4-methoxy-benzenemethanethiol (0.72 g).

MS (ESI) 350 (M+H, 100%).

b) 4-Bromo-2-[[(3-chloro4-methoxyphenyl)methyl]thio]-7(8H)-pteridinone

The subtitled compound (0.28 g) was prepared by the method of Example 3, step (b) using the product from example 11, step (a) (1.25 g).

MS (ESI) 411/413 (M–H, 100%).

c) 2-[[(3-Chloro-4-methoxyphenyl)methyl]thio]-4-[[2-hydroxy-1-(hydroxymethyl)ethyl]amino]-7(8H)-pteridinone The titled compound (89 mg) was prepared by the method of Example 8 using the product from example 11, step (b) (0.100 g).

m.p. 209–211°

MS (APCI) 424 (M+H, 100%).

$^1$H NMR: δ (DMSO) 12.73 (1H, s), 7.85 (1H, s), 7.54 (1H, d), 7.45 (2H, m), 7.06 (1H, d), 4.81 (2H, br), 4.33 (2H, s), 4.20–4.28 (1H, m), 3.82 (3H, s), 3.51–3.63 (4H, m).

EXAMPLE 12

4-[(2-Aminoethyl)amino]-2-[[(3-chloro-4-methoxyphenyl)methyl]thio]-7(8H)-pteridinone, monotrifluoroacetate The titled compound (15 mg) was prepared by the method of Example 2, step (f) using the product from Example 11 step (b) (50 mg) and ethylenediamine (24μl). The reaction mixture was diluted with water (150 ml), lyophilised to give a solid, and purified (HPLC, Symmetry® C8 column, 0.1% aqueous trifluoroacetic acid:acetonitrile, isocratic elution 75:25).

MS (APCI) 393 (M+H parent amine, 100%).

$^1$H NMR: δ ($D_2O$) 7.89 (1H, s), 7.39 (1H, s), 7.28 (1H, d), 6.92 (1H, d), 4.23 (2H, s), 3.84 (5H, m), 3.25 (2H, br t).

EXAMPLE 13

2-[[(2-Fluoro-4-methoxyphenyl)methyl]thio]-4-[[(1R)-2-hydroxy-1-methylethyl]amino]-7(8,H)-pteridinone a) 2-[[(2,3-Difluorophenyl)methyl]sulfonyl]-4-[[(1R)-2-hydroxy-1-methylethyl]amino]-7(8H)-pteridinone 2-[[(2,3-Difluorophenyl)methyl]thio]-4-[[(1R)-2-hydroxy-1-methylethyl]amino]-7(8H)-pteridinone (0.38 g) was stirred in acetonitrile (150 ml) and water (150 ml) with oxone (3.79 g) for 18 hrs. Acetonitrile was removed in vacuo to leave an aqueous suspension. The solid was collected and dried in vacuo to afford the subtitled compound (0.30 g).

MS (APCI) 412 (M+H) (100%)

b) 2-Fluoro4-methoxy-benzenemethanethiol

The subtitled compound (0.33 g) was prepared by the method of Example 6, step (c) using 1-(chloromethyl)-2-fluoro-4-methoxy-benzene (0.56 g).

MS (EI) 172 (M+), 139 (100%).

c) 2-[[(2-Fluoro-4-methoxyphenyl)methyl]thio]-4-[[(1R)-2-hydroxy-1-methylethyl]amino]-7(8H)-pteridinone The titled compound was prepared by the method of Example 6, step (d) using the product from example 13, step (a) (0.20 g), the product from example 13, step (b) (0.10 g) and DMSO (2 ml) instead of NMP as solvent. The reaction mixture was purified (HPLC, Symmetry® C8 column, 0.1% aqueous ammonium acetate:acetonitrile, gradient elution 80:20 to 20:80) to give a white solid (63 mg).

MS (APCI) 392 (M+H, 100%).

$^1$H NMR: δ (DMSO) 12.69 (1H, br s), 7.83 (1H, s), 7.75 (1H, br d), 7.53 (1H, t), 6.83 (1H, d), 6.72 (1H, d), 4.83 (1H, br t), 4.34 (3H, m), 3.75 (3H, s), 3.41–3.54 (2H, m), 1.16 (3H, d).

EXAMPLE 14

2-[[(2-Fluoro-3-methylphenyl)methyl]thio]-4-[[(1R)-2-hydroxy-1-methylethyl]amino]-7(8H)-pteridinone a) 2-Fluoro-3-methyl-benzenemethanethiol The subtitled compound (0.36 g) was prepared by the method of Example 6, step (c) using 2-fluoro-3-methyl-benzyl bromide (0.55 g).

MS (EI) 156 (M+), 123 (100%).

b) 2-[[(2-Fluoro-3-methylphenyl)methyl]thio]-4-[[(1R)-2-hydroxy-1-methylethyl]amino]-7(8H)-pteridinone The titled compound (56 mg) was prepared by the method of Example 13, step (c) using the product from Example 13, step (a) (0.20 g) and the product from example 14, step (a) (94 mg).

MS (APCI) 376 (M+H, 100%).

$^1$H NMR: δ (DMSO) 12.69 (1H, br s), 7.83 (1H, s), 7.76 (1H, d), 7.43 (1H, t), 7.18 (1H, t), 7.02 (1H, t), 4.83 (1H, t), 4.28–4.43 (3H, m), 3.41–3.54 (2H, m), 2.23 (3H, s), 1.15 (3H, d).

EXAMPLE 15

2-[[(3-Fluoro-2-methoxyphenyl)methyl]thio]-4-[[(1R)-2-hydroxy-1-methylethyl]amino]-7(8H)-pteridinone a) 1-(Chloromethyl)-3-fluoro-2-methoxy-benzene A solution of 3-fluoro-2-methoxy-benzenemethanol (WO 20000419) (0.50 g) and thionyl chloride (0.47 ml) in dichloromethane (30 ml) was stirred for 2 hours then concentrated in-vacuo to give the subtitled compound, which was used directly in the next step.

b) 3-Fluoro-2-methoxy-benzenemethanethiol

The subtitled compound (0.31 g) was prepared by the method of Example 6, step (c) using the product from example 15, step (a).

MS (EI) 172 (M+), 139 (100%).

c) 2-[[(3-Fluoro-2-methoxyphenyl)methyl]thio]-4-[[(1R)-2-hydroxy-1-methylethyl]amino]-7(8H)-pteridinone The titled compound (84 mg) was prepared by the method of Example 13, step (c) using the product from Example 13, step (a) (0.20 g) and the product from example 15, step (b) (0.10 g).

MS (APCI) 392 (M+H, 100%).

$^1$H NMR: δ (DMSO) 12.69 (1H, br s), 7.83 (1H, s), 7.76 (1H, d), 7.37 (1H, d), 7.18 (1H, m), 7.03 (1H, m), 4.83 (1H, br t), 4.31–4.42 (3H, m), 3.91 (3H, s), 3.42–3.53 (2H, m), 1.16 (3H, d).

EXAMPLE 16

2-[[[4-(Difluoromethoxy)phenyl]methyl]thio]-4-[[(1R)-2-hydroxy-1-methylethyl]amino]-7(8H)-pteridinone a) 4-(Difluoromethoxy)-benzenemethanethiol The subtitled compound (0.20 g) was prepared by the method of Example 6, step (c) using 4-(difluoromethoxy)-benzyl bromide (0.53 g).

MS (EI) 190 (M+), 107 (100%).

b) 2-[[[4-(Difluoromethoxy)phenyl]methyl]thio]-4-[[(1R)-2-hydroxy-1-methylethyl]amino]-7(8H)-pteridinone The titled compound (51 mg) was prepared by the method of Example 13, step (c) using the product from Example 13, step (a) (0.20 g) and the product from example 16, step (a) (0.17 g).

MS (APCI) 410 (M+H, 100%).

$^1$H NMR: δ (DMSO) 12.67 (1H, br s), 7.82 (1H, s), 7.74 (1H, d), 7.53 (2H, d), 7.19 (1H, t), 7.10 (2H, d), 4.82 (1H, t), 4.28–4.41 (3H, m), 3.39–3.52 (2H, m), 1.15 (3H, d).

EXAMPLE 17

4-[[(1R)-2-Hydroxy-1-methylethyl]amino]-2-[[(4-hydroxyphenyl)methyl]thio]-7(8H)-pteridinone The titled compound (8 mg) was obtained as a by-product during the preparation of Example 16.

MS (APCI) 360 (M+H, 100%).

$^1$H NMR: δ (DMSO) 12.60 (1H, br), 9.35 (1H, s), 7.81 (1H, s), 7.70 (1H, d), 7.24 (2H, d), 6.68 (2H, d), 4.83 (1H, t), 4.23–4.36 (3H, m), 3.44–3.55 (2H, m), 1.17 (3H, d).

EXAMPLE 18

4-[[(1R)-2-Hydroxy-1-methylethyl]amino]-2-[[(3-methylphenyl)methyl]thio]-7(8H)-pteridinone The titled compound (75 mg) was prepared by the method of Example 13, step (c) using the product from Example 13, step (a) (0.20 g) and 3-methyl-benzenemethanethiol (75 mg).

MS (APCI) 358 (M+H, 100%).

$^1$H NMR: δ (DMSO) 12.66 (1H, br s), 7.82 (1H, s), 7.73 (1H, br d), 7.16–7.26 (3H, m), 7.05 (1H, br d), 4.82 (1H, br t), 4.34 (3H, m), 3.40–3.54 (2H, m), 2.28 (3H, s), 1.17 (3H, br d).

EXAMPLE 19

2-[(1,3-Benzodioxol-4-ylmethyl)thio]-4-[[(1R)-2-hydroxy-1-methylethyl]amino]-7(8H)-pteridinone a) 1,3-Benzodioxole-4-methanethiol The subtitled compound (0.29 g) was prepared by the method of Example 6, step (c) using 4-(bromomethyl)-1,3-benzodioxole (0.51 g).

MS (EI) 168 (M+), 135 (100%).

b) 2-[(1,3-Benzodioxol-4-ylmethyl)thio]-4-[[(1R)-2-hydroxy-1-methylethyl]amino]-7(8H)-pteridinone The titled compound (57 mg) was prepared by the method of Example 13, step (c) using the product from Example 13, step (a) (0.20 g) and the product from example 19, step (a) (0.10 g).

MS (APCI) 388 (M+H, 100%).

$^1$H NMR: δ (DMSO) 12.66 (1H, br s), 7.82 (1H, s), 7.75 (1H, br d), 6.99 (1H, d), 6.80 (2H, m), 6.04 (2H, s), 4.82 (1H, t), 4.33 (3H, m), 3.41–3.55 (2H, m), 1.16 (3H, d).

EXAMPLE 20

2-[[(2,4-Difluorophenyl)methyl]thio]-4-[[(1R)-2-hydroxy-1-methylethyl]amino]-7(8H)-pteridinone a) 2,4-Difluoro-benzenemethanethiol The subtitled compound (0.35 g) was prepared by the method of Example 6, step (c) using 2,4-difluoro-benzyl bromide (0.55 g).

MS (EI) 160 (M+), 127 (100%).

b) 2-[[(2,4-Difluorophenyl)methyl]thio]-4-[[(1R)-2-hydroxy-1-methylethyl]amino]-7(8H)-pteridinone The titled compound (77 mg) was prepared by the method of Example 13, step (c) using the product from Example 13, step (a) (0.20 g) and the product from example 20, step (a) (87 mg).

MS (APCI) 380 (M+H, 100%).

$^1$H NMR: δ (DMSO) 12.70 (1H, br), 7.83 (1H, s), 7.67–7.76 (2H, m), 7.24 (1H, br t), 7.03 (1H, br t), 4.82 (1H, br), 4.30–4.37 (3H, m), 3.43–3.49 (2H, m), 1.15 (3H, br d).

EXAMPLE 21

2-[[(3-Chlorophenyl)methyl]thio]-4-[[(1R)-2-hydroxy-1-methylethyl]amino]-7(8H)-pteridinone The titled compound (66 mg) was prepared by the method of Example 13, step (c) using the product from Example 13, step (a) (0.20 g) and 3-chloro-benzenemethanethiol (92 mg).

MS (APCI) 378 (M+H, 100%).

$^1$H NMR: δ (DMSO) 12.70 (1H, br s), 7.82 (1H, s), 7.74 (1H, br d), 7.55 (1H, s), 7.45 (1H, br d), 7.34 (2H, m), 4.81 (1H, br t), 4.31–4.43 (3H, m), 3.43–3.50 (2H, m), 1.15 (3H, br d).

EXAMPLE 22

4-[[(1R)-2-Hydroxy-1-methylethyl]amino]-2-[(5-isoxazolylmethyl)thio]-7(8H)-pteridinone The titled compound (0.038 g) was prepared by the method of Example 13, step (c) using the product from Example 13, step (a) (0.10 g) and 5-isoxazolylmethylmercaptan (0.057 g).

Mp 191–194° C.

MS (APCI) 335 (M+H, 100%).

$^1$H NMR: δ (DMSO) 12.71 (1H, br s), 8.47 (1H, s), 7.84 (1H, s), 7.80 (1H, d), 6.51 (1H, s), 4.81 (1H, t), 4.54 (2H, q), 4.26 (1H, m), 3.44 (2H, m), 1.13 (3H, d).

EXAMPLE 23

4-[[-2-Hydroxy-1-(hydroxymethylethyl]amino]-2-[(5-isoxazolylmethyl)thio]-7(8H)-pteridinone a) 2-[[(2,3-Difluorophenyl)methyl]sulfonyl]-4-[[-2-hydroxy-1-hydroxymethylethyl]amino]-7(8H)-pteridinone 2-[[(2,3-Difluorophenyl)methyl]thio]-4-[[-2-hydroxy-1-hydroxymethylethyl]amino]-7(8H)-pteridinone (2.25 g) was stirred in acetonitrile (750 ml) and water (750 ml) with oxone (22.5 g) for 18 hrs. Acetonitrile was removed in vacuo to leave an aqueous suspension. The mixture was extracted into ethyl acetate. The combined extracts were washed with saturated sodium chloride solution, dried (MgSO$_4$) and the solvent removed in vacuo to afford the subtitled compound (1.92 g).

MS (APCI) 428 (M+H)(100%)

b) 4-[[-2-Hydroxy-1-(hydroxymethylethyl]amino]-2-[(5-isoxazolylmethyl) thio]-7(8H)-pteridinone The titled compound (0.03 g) was prepared by the method of Example 13, step (c) using the product from example 23, step (a) (0.20 g) and 5-isoxazolylmethylmercaptan (0.1 g).

mp 199–203° C.

MS (APCI) 351 (M+H, 100%).

$^1$H NMR: δ (DMSO) 8.47(1H, s), 7.86 (1H, s), 7.54(1H , d), 6.55 (1H , s), 4.80 (2H, t), 4.56 (2H, s), 4.22 (1H, m), 3.55 (4H, m).

EXAMPLE 24

4-[[(1R)-2-Hydroxy-1-methylethyl]amino]-2-[[(5-methyl-2-furanyl)methyl]thio]-7(8H)-pteridinone The titled compound (0.058 g) was prepared by the method of Example 13, step (c) using the product from Example 13, step (a) (0.20 g) and 5-methyl-2-furanylmethylmercaptan (0.15 g of 80% pure).

Mp 197–199° C.

MS (APCI) 348 (M+H, 100%).

$^1$H NMR: δ (DMSO) 12.65 (1H, br s), 7.82 (1H, s), 7.74 (1H, d), 6.27 (1H, d), 5.96 (1H, d), 4.83 (1H, t), 4.37 (2H, s), 4.32 (1H, m), 3.47 (2H, m), 2.22 (3H, s), 1.17 (3H, d).

EXAMPLE 25

2-[[(2-Fluorophenyl)methyl]thio]-4-[[(1R)-2-hydroxy-1-methylethyl]amino]-7(8H)-pteridinone The titled compound (0.089 g) was prepared by the method of Example 13, step (c) using the product from Example 13, step (a) (0.20 g) and 2-fluorobenzylmercaptan (0.083 g).

Mp 203–205° C.

MS (APCI) 362 (M+H, 100%).

$^1$H NMR: δ (DMSO) 12.69 (11H, br s), 7.83 (1H, s), 7.75 (1H, d), 7.64 (1H, m), 7.32 (1H, m), 7.20 (1H, m), 7.14 (1H, m), 4.82 (1H, t), 4.41 (2H, q), 4.31 (1H, m), 3.47 (2H, m) 1.15 (3H, d).

EXAMPLE 26

4-[[(1R)-2-Hydroxy-1-methylethyl]amino]-2-[[(2-thienyl)methyl)thio]-7(8H)-pteridinone The titled compound (0.076 g) was prepared by the method of Example 13, step (c) using the product from Example 13, step (a) (0.20 g) and 2-thienylmethylmercaptan (0.050 g).

Mp 209–212° C.

MS (APCI) 350 (M+H, 100%).

$^1$H NMR: δ (DMSO) 12.66 (1H, br s), 7.83 (1H, s), 7.77 (1H, d), 7.37 (1H, d), 7.12 (1H, d), 6.93 (1H, dd), 4.82 (1H, t), 4.62 (2H, q), 4.36 (1H, m), 3.46 (2H, m), 1.17 (3H, d).

EXAMPLE 27

2-[[(2-Fluorophenyl)methyl]thio]-4-[[-2-hydroxy-1-(hydroxymethylethyl]amino]-7(8H)-pteridinone The titled compound (0.088 g) was prepared by the method of Example 13, step (c) using the product from example 23 step (a) (0.21 g) and 2-fluorobenzylmercaptan (0.83 g).

mp 206–208° C.

MS (APCI) 378 (M+H, 100%).

$^1$H NMR: δ (DMSO) 12.67 (1H,br s), 7.84 (1H, s), 7.66 (1H, t), 7.47 (1H, d), 7.32 (1H, m), 7.16 (2H, m), 4.80 (2H, t), 4.41 (2H, s), 4.25 (1H, m), 3.57 (4H, m).

EXAMPLE 28

4-[[-2-Hydroxy-1-(hydroxymethyl)ethyl]amino]-2-[(2-thienylmethyl)thio]-7(8H)-pteridinone The titled compound (0.075 g) was prepared by the method of Example 13, step (c) using the product from example 23, step (a) (0.21 g) and 2-thienylmethylmercaptan (0.05 g).

mp 220–223° C.

MS (APCI) 366 (M+H, 100%).

$^1$H NMR: δ (DMSO) 12.67 (1H,br s), 7.85 (1H, s), 7.49 (1H, d), 7.38 (1H, d), 7.15 (1H, d), 6.93 (1H, dd), 4.81 (2H, t), 4.64 (2H, s), 4.28 (1H, m), 3.59 (4H, m).

EXAMPLE 29

2-[[(2-Fluoro-5-methylphenyl)methyl]thio]-4-[[(1R)-2-hydroxy-1-methylethyl]amino]-7(8H)-pteridinone a) 2-Fluoro-5-methyl-benzenemethanethiol, acetate Diisopropylazodicarboxylate (2.68 ml) was added to a solution of triphenylphosphine (3.57 g) in dry THF (30 ml) at 0° C. The mixture was stirred for 1 hr. A solution of 2-fluoro-5-methyl-benzenemethanol (0.96 ml) in dry THF (10 ml) was added dropwise over 40 mins. The mixture was stirred for 1 hr then warmed to room temp and stirred for a further 3 hrs. The solvent was evaporated and the residue slurried with ether and filtered. The filtrate was evaporated and purified by column chromatography, eluting with 3% ethyl acetate in isohexane to give the subtitled compound as an oil (1.23 g).

GC/MS 100% (EI) 198 (M+), 123 (100%)

b) 2-Fluoro-5-methyl-benzylmethanethiol

2-Fluoro-5-methyl-benzenemethanethiol acetate (1.2 g) was stirred in methanol previously saturated with ammonia (10 ml) at room temp for 30 mins. The solvent was evaporated and the residue partitioned between ether and water. The layers were separated and the water extracted with ether. The combined ether was washed with water, dried and evaporated to leave an oil (0.9 g).

GC/MS 97% (EI) 156(M+) 123(100%)

(c) 2-[[(2-Fluoro-5-methylphenyl)methyl]thio]-4-[[(1R)-2-hydroxy-1-methylethyl]amino]-7(8H)-pteridinone The titled compound (0.093 g) was prepared by the method of Example 13, step (c) using the product from Example 13, step (a) (0.20 g) and the product from example 29, step (b).

Mp 202–204° C.

MS (APCI) 376 (M+H, 100%).

$^1$H NMR: δ (DMSO) 12.68 (1H, br s), 7.82 (1H, s), 7.74 (1H, d), 7.41 (1H, d), 7.07 (2H, m), 4.83 (1H, t), 4.33 (3H, m), 3.49 (2H, m), 2.25 (3H, s), 1.17 (3H, d).

EXAMPLE 30

2-[[(2-Fluoro-3-(trifluoromethyl)phenyl)methyl]thio]-4-[[(1R)-2-hydroxy-1-methylethyl]amino]-7(8H)-pteridinone a) 4-(1-Methylethoxy)-2-[[[3-(trifluoromethyl)phenyl]methyl]thio]-7(8H)-pteridinone 6-[[[2-Fluoro-3-(trifluoromethyl)phenyl]methyl]thio]-2-[[[3-(trifluoromethyl)phenyl]methyl]thio]-4,5-pyrimidinediamine (7.12 g) was added to a solution of sodium methoxide prepared from sodium (0.62 g) and methanol (150 ml). Ethyl glyoxalate (6.5 ml of 50% in toluene) was added and the mixture heated under reflux for 30 mins. The solvent was evaporated and redissolve in 2-propanol. Sodium (1.1 g) was added and the mixture heated under reflux for 30 mins. The solvent was evaporated and the residue taken up in water and acidified with dilute hydrochloric acid. The mixture was extracted with dichloromethane and the extracts washed with water then dried (MgSO$_4$), and evaporated. Purification by flash chromatography eluting with 10% ethyl acetate in dichloromethane to give the subtitled compound as an solid (2.64 g).

mp 205–206° C.

MS (APCI) 415(M+H, 100%)

$^1$H NMR: δ (DMSO) 13.03 (1H, s), 8.06 (1H, t), 7.97 (1H, s), 7.70 (1H, t), 7.38 (1H, t), 5.38 (1H, m), 4.53 (2H, s), 1.31 (6H, d).

b) 2-[[(2-Fluoro-3-(trifluoromethyl)phenyl)methyl]thio]-4-[[(1R)-2-hydroxy-1-methylethyl]amino]-7(8H)-pteridinone The product from example 30, step (a) (0.3 g) and D-alaninol (0.6 ml) were sonicated with N-methylimidazole (1 ml) to form a paste. The paste was heated in a 300W microwave at 160° C. for 25 mins. Solvent was removed by bulb to bulb distillation and the residue purified by reverse phase HPLC to give the title compound (0.52 g).

Mp 217–219° C.

MS (APCI) 430 (M+H, 100%)

$^1$H NMR: δ (DMSO) 8.03 (1H, t), 7.83 (1H, s), 7.76 (1H, d), 7.68 (1H, t), 7.35 (1H, t) 4.82 (1H, t), 4.47 (2H, q), 4.26 (1H, m), 3.45 (2H, m), 1.12 (3H, d).

EXAMPLE 31

2-[[(2-Fluoro-3-(trifluoromethyl)phenyl)methyl]thio]-4-[[2-hydroxy-1-(hydroxymethyl)ethyl]amino]-7(8H)-pteridinone The titled compound (0.049 g) was prepared by the method of Example 30, step (b) using the product from Example 30, step (a) (0.30 g) and 2-aminopropane-1,3-diol (0.66 g).

Mp 244–245° C.

MS (APCI) 446 (M+H, 100%).

$^1$H NMR: δ (DMSO) 12.76 (1H, s), 8.06 (1H, t), 7.85 (1H, s), 7.68 (1H, t), 7.52 (1H, d), 7.35 (1H, t), 4.81 (2H, t), 4.47 (2H, s), 4.23 (1H, m), 3.55 (4H, m).

EXAMPLE 32

2-[[(2-Fluoro-3-(trifluoromethyl)phenyl)methyl]thio]-4-[(2-hydroxyethyl)amino]-7(8H)-pteridinone The titled compound (0.072 g) was prepared by the method of Example 30, step (b) using the product from Example 30, step (a) (0.30 g) and ethanolamine (0.5 ml)

Mp 221–222° C.

MS (APCI) 416 (M+H, 100%).

$^1$H NMR: δ (DMSO) 12.73 (1H, s), 8.08 (1H, m), 7.03 (1H, t), 7.85 (1H, s), 7.68 (1H, t), 7.36 (1H, t), 4.78 (1H, t), 4.47 (2H, s), 3.52 (4H, m).

EXAMPLE 33

4-[(2-aminoethyl)amino]-2-[[(2-fluoro-3-(trifluoromethyl)phenyl)methyl]thio]-7(8H)-pteridinone The titled compound (0.054 g) was prepared by the method of Example 30, step (b) using the product from Example 30, step (a) (0.30 g) and ethylenediamine (0.5 ml). The product was purified by crystallisation from methanol.

MS (APCI) 415 (M+H, 100%).

$^1$H NMR: δ (DMSO) 8.01 (1H, t), 7.91 (1H, br s), 7.67 (1H, m), 7.58 (1H, br s), 7.52 (1H, bs), 7.35 (1H, t), 7.17 (1H, br s), 4.45 (2H, s), 3.42 (2H,t), 3.15 (2H, br s), 2.75 (8H, m).

EXAMPLE 34

2-[[(2,3-Difluorophenyl)methyl]thio]-4-[[2-hydroxy-1-(hydroxymethyl)-1-methylethyl]amino]-7(8H)-pteridinone The product of example 2, step (e) (400 mg) was dissolved in N-methylpyrrolidinone (15 ml), and Hunigs base (0.36 ml) was added followed by 2-amino-2-methyl-1,3-propanediol (0.273 g). The mixture was stirred at 110° C. for 17 hours. The resulting mixture was poured in to water, and allowed to stand overnight to allow a solid to precipitate out. This solid was collected by filtration, then purified by reverse phase preparative HPLC on symmetry C-8®, using 10 to 95% acetonitrile in 0.1% aqueous ammonium acetate at 20 ml/min over 10 min to give the title compound as off white needles (0.113 g).

MS: APCI (+ve) 410 (M+H)

$^1$H NMR: δ (DMSO) 1.30 (3H, s), 3.54–3.58 (2H, m), 3.63–3.67 (2H, m), 4.45 (2H, s) 4.98–5.01 (2H, t), 7.13 (1H, s), 7.15–7.19 (1H, m), 7.31–7.36 (1H, m), 7.45–7.49 (1H, t), 7.84 (1H, s), 12.74 (1H, bs).

EXAMPLE 35

2-[[(2,3-Difluorophenyl)methyl]thio]-4-[[(1R)-2-hydroxy-1-methylethyl]amino]-6-methyl-7(8H)-pteridinone a) 4-Amino-2-[[(2,3-difluorophenyl)methyl]thio]-6-methyl-7(8H)-pteridinone The sub-titled compound was prepared from the product of Example 2, step (b) (2 g) and triethylphosphonopropionate (3.2 g) using the method of Example 3, step (a).

MS: APCI (+ve) 336 (M+1)

$^1$H NMR: δ (DMSO) 2.33 (s,3H), 4.40 (s,2H), 7.09–7.58 (m,3H), 12.56 (bs,1H).

b) 4-Bromo-2-[[(2,3-difluorophenyl)methyl]thio]-6-methyl-7(8H)-pteridinone

The sub-titled compound was prepared from the product of example 35, step (a) (1.5 g) and bromoform (30 ml) using the method of Example 3, step (b).

MS: APCI (+ve) 400 (M+1)

$^1$H NMR: δ (DMSO) 2.39 (s,3H), 4.52 (s,2H), 7.11–7.55 (m,3H), 13.21 (bs,1H).

c) 2-[[(2,3-Difluorophenyl)methyl]thio]-4-[[(1R)-2-hydroxy-1-methylethyl]amino]-6-methyl-7(8H)-pteridinone The titled compound was prepared from the product of example 35, step (b) (200 mg) and D-alaninol (120 μl) using the method of Example 2, step (f).

MS: APCI (+ve) 394 (M+1)

$^1$H NMR: δ (DMSO) 1.12 (d,3H), 2.34 (s,3H), 3.45 (m,2H,), 4.24 4.33 (m,1H), 4.43 (s,2H), 4.85 (bs,1H), 7.10–7.49 (m,3H), 12.58 (s,1H).

EXAMPLE 36

2-[[(2,3-Difluorophenyl)methyl]thio]-7,8-dihydro-4-[[(1R)-2-hydroxy-1-methylethyl]amino]-7-oxo-6-pteridinecarboxylic acid ethyl ester a) 4-Amino-2-[[(2,3-difluorophenyl)methyl]thio]-7,8-dihydro-7-oxo-6-pteridinecarboxylic acid ethyl ester The product of Example 2, step (b) (5 g) was dissolved in diethyl malonate (100 ml) and heated to 120° C. for 10 hr, with stirring. The reaction mixture was allowed to cool and the solid that precipitated was filtered, washed with water and dried in the oven at 50° C. to yield the product as a yellow solid (3.2 g).

MS: APCI (+ve) 394 (M+1)

$^1$H NMR: δ (DMSO) 1.29–1.33 (t,3H), 4.28–4.35 (q,2H), 4.42 (s,2H) 7.11–7.59 (m,3H), 7.88 (bs,1H), 8.08 (bs,1H), 13.05 (s,1H).

b) 4-Bromo-2-[[(2,3-difluorophenyl)methyl]thio]-7,8-dihydro-7-oxo-6-pteridinecarboxylic acid ethyl ester The sub-titled compound was prepared from the product of example 36, step (a) (2 g) and bromoform (40 ml) using the method of Example 3, step (b).

MS: APCI (+ve) 458 (M+1)

$^1$H NMR: δ (DMSO) 1.31 (t,3H), 4.40 (q,2H), 4.52 (s,2H), 7.13–7.55 (m,3H), 13.05 (s,1H).

c) 2-[[(2,3-Difluorophenyl)methyl]thio]-7,8-dihydro-4-[[(1R)-2-hydroxy-1-methylethyl]amino]-7-ox-6-pteridinecarboxylic acid ethyl ester The titled compound was prepared from the product of example 36, step (b) (300 mg) and D-alaninol (180 μl) using the method of Example 2, step (f).

MS: APCI (+ve) 451 (M+1)

$^1$H NMR: δ (DMSO) 1.12 (d,3H), 1.29 (t,3H), 3.41–3.53 (m,2H), 4.22–4.32 (m,3H), 4.51 (s,2H), 4.83–4.86 (t,1H), 7.07–7.47 (m,3H).

EXAMPLE 37

2-[[(2,3-Difluorophenyl)methyl]thio]-4-[[(1R)-2-hydroxy-1-methylethyl]amino]-6-(trifluoromethyl)-7(8H)-pteridinone a) 4-Amino-2-[[(2,3-difluorophenyl)methyl]thio]-6-(trifluoromethyl)-7(8H)-pteridinone The sub-titled compound was prepared from the product of Example 2, step (c) (5 g) and trifluoropyruvate (10 ml) using the method of Example 2, step (d).

MS: APCI (+ve) 390 (M+1)

$^1$H NMR: δ (DMSO) 4.32 (s,2H), 7.10–7.70 (m,3H), 7.92–8.23 (2bs,2H), 13.23 (bs,1H)

b) 4-Bromo-2-[[(2,3-difluorophenyl)methyl]thio]-6-(trifluoromethyl)-7(8H)-pteridinone The sub-titled compound was prepared from the product of example 37, step (a) (1.5 g) and bromoform (30 ml) using the method of Example 3, step (b).

MS: APCI (+ve) 454 (M+1).

c) 2-[[(2,3-Difluorophenyl)methyl]thio]-4-[[(1R)-2-hydroxy-1-methylethyl]amino]-6-(trifluoromethyl)-7(8,H)-pteridinone The titled compound was prepared from the product of example 37, step (b) (150 mg) and D-alaninol (100 μl) using the method of Example 2, step (f).

MS: APCI (+ve) 448 (M+1)

$^1$H NMR: δ (DMSO) 1.15 (d,3H), 3.50 (m,2H), 4.37 (m,1H), 4.47 (s,2H), 4.89 (t,1H), 7.12–7.49 (m,3H), 7.79 (d,1H), 13.25 (bs,1H).

EXAMPLE 38

2-[[(2,3-Difluorophenyl)methyl]thio]-4-[[(1R)-2-hydroxy-1-methylethyl]amino]-7(8H)-pteridinone sodium salt The product from example 2, step (f) was suspended in water containing one equivalent of sodium hydroxide, followed by the addition of a small aliquot of tetrahydrofuiran and methanol to aid dissolution. The resultant solution was then lyopholised to give the title compound as a colourless solid.

m.p. 255–260° C. (dec)

MS: APCI (+ve) 380 (M+1)

$^1$H NMR: δ (DMSO) 7.42 (1H, m), 7.37 (1H, s), 7.31 (1H, m), 7.13 (1H, m), 6.89 (1H, d), 4.79 (1H, t), 4.40 (2H, s), 4.15 (1H, m), 3.45 (2H, m), 1.12 (3H, d).

EXAMPLES 39–72

Examples 39 to 72 were prepared by heating the product of example 2, step (e) (2.5×10$^{-6}$ moles) with the appropriate amine (2 equivalents) and N-ethyldiisopropylamine (6 equivalents) in N-methylpyrrolidinone (0.25 ml) in a sealed vessel at 100° C. for 1 hour.

EXAMPLE 39

2-[(2,3-difluorobenzyl)thio]-4-(ethylamino)-7(8H)-pteridinone

MS: APCI (+ve) 350 (M+1).

EXAMPLE 40

2-[(2,3-difluorobenzyl)thio]-4-(isopropylamino)-7(8H)-pteridinone

MS: APCI (+ve) 364 (M+1).

EXAMPLE 41

(+/−)-4-(sec-butylamino)-2-[(2,3-difluorobenzyl)thio]-7(8H)-pteridinone

MS: APCI (+ve) 378 (M+1).

EXAMPLE 42

2-({2-[(2,3-difluorobenzyl)thio]-7-oxo-7,8-dihydro-4-pteridinyl}amino)acetamide

MS: APCI (+ve) 379 (M+1).

EXAMPLE 43

(+/−)-2-[(2,3-difluorobenzyl)thio]-4-[(2-hydroxypropyl)amino]-7(8H)-pteridinone

MS: APCI (+ve) 380 (M+1).

EXAMPLE 44

(S)-2-[(2,3-difluorobenzyl)thio]-4-[(2-hydroxy-1-methylethyl)amino]-7(8H)-pteridinone MS: APCI (+ve) 380 (M+1).

EXAMPLE 45

(+/−)-2-[(2,3-difluorobenzyl)thio]-4-[(2-hydroxy-1-methylethyl)amino]-7(8H)-pteridinone MS: APCI (+ve) 380 (M+1).

EXAMPLE 46

(R)-2-[(2,3-difluorobenzyl)thio]-4-[(2-hydroxypropyl)amino]-7(8H)-pteridinone

MS: APCI (+ve) 380 (M+1).

EXAMPLE 47

2-[(2,3-difluorobenzyl)thio]-4-[(3-hydroxypropyl)amino]-7(8H)-pteridinone

MS: APCI (+ve) 380 (M+1).

EXAMPLE 48

2-[(2,3-difluorobenzyl)thio]-4-[(2-hydroxyethyl)(methyl)amino]-7(8H)-pteridinone MS: APCI (+ve) 380 (M+1).

EXAMPLE 49

3-[{2-[(2,3-difluorobenzyl)thio]-7-oxo-7,8-dihydro-4-pteridinyl}(methyl)amino]propanenitrile MS: APCI (+ve) 389 (M+1).

EXAMPLE 50
(R)-2-[(2,3-difluorobenzyl)thio]-4-{[1-(hydroxymethyl)propyl]amino}-7(8m)-pteridinone
MS: APCI (+ve) 394 (M+1).

EXAMPLE 51
(S)-2-[(2,3-difluorobenzyl)thio]4-{[1-(hydroxymethyl)propyl]amino}-7(8H)-pteridinone
MS: APCI (+ve) 394 (M+1).

EXAMPLE 52
2-[(2,3-difluorobenzyl)thio]-4-[(4-hydroxybutyl)amino]-7(8H)-pteridinone
MS: APCI (+ve) 394 (M+1).

EXAMPLE 53
(+/−)-2-[(2,3-difluorobenzyl)thio]-4-{[1-(hydroxymethyl)propyl]amino}-7(8H)-pteridinone
MS: APCI (+ve) 394 (M+1).

EXAMPLE 54
2-[(2,3-difluorobenzyl)thio]-4-[(2-hydroxy-1,1-dimethylethyl)amino]-7(8H)-pteridinone
MS: APCI (+ve) 394 (M+1).

EXAMPLE 55
2-[(2,3-difluorobenzyl)thio]-4-[ethyl(2-hydroxyethyl)amino]-7(8H)-pteridinone
MS: APCI (+ve) 394 (M+1).

EXAMPLE 56
(+/−)-4-[(3-amino-2-hydroxypropyl)amino]-2-[(2,3-difluorobenzyl)thio]-7(8H)-pteridinone
MS: APCI (+ve) 395 (M+1).

EXAMPLE 57
(+/−)-2-[(2,3-difuorobenzyl)thio]-4-[(1,3-dimethylbutyl)amino]-7(8H)-pteridinone
MS: APCI (+ve) 406 (M+1).

EXAMPLE 58
(1R,2R)-2-[(2,3-difluorobenzyl)thio]-4-[(2-hydroxycyclopentyl)amino]-7(8H)-pteridinone
MS: APCI (+ve) 406 (M+1).

EXAMPLE 59
2-[(2,3-difluorobenzyl)thio]-4-[(5-hydroxypentyl)amino]-7(8H)-pteridinone
MS: APCI (+ve) 408 (M+1).

EXAMPLE 60
(+/−)-2-[(2,3-difluorobenzyl)thio]-4-{[1-(hydroxymethyl)butyl]amino}-7(8H)-pteridinone
MS: APCI (+ve) 408 (M+1).

EXAMPLE 61
(+/−)-methyl 2-({2-[(2,3-difluorobenzyl)thio]-7-oxo-7,8-dihydro-4-pteridinyl}amino)propionate
MS: APCI (+ve) 408 (M+1).

EXAMPLE 62
2-[(2,3-difuorobenzyl)thio]-4-[(3-hydroxy-2,2-dimethylpropyl)amino]-7(8H)-pteridinone
MS: APCI (+ve) 408 (M+1).

EXAMPLE 63
(1R,2R)-2-[(2,3-difluorobenzyl)thio]-4-{[2-hydroxy-1-(hydroxymethyl)propyl]amino}-7(8H)-pteridinone
MS: APCI (+ve) 410 (M+1).

EXAMPLE 64
4-[bis(2-hydroxyethyl)amino]-2-[(2,3-difluorobenzyl)thio]-7(8H)-pteridinone
MS: APCI (+ve) 410 (M+1).

EXAMPLE 65
2-[(2,3-difluorobenzyl)thio]4-{[2-(2-hydroxyethoxy)ethyl]amino}-7(8H)-pteridinone
MS: APCI (+ve) 410 (M+1).

EXAMPLE 66
2-[(2,3-difluorobenzyl)thio]-4-[(2,2-dimethoxyethyl)amino]-7(8H)-pteridinone
MS: APCI (+ve) 410 (M+1).

EXAMPLE 67
4-{[2-(diethylamino)ethyl]amino}-2-[(2,3-difluorobenzyl)thio]-7(8H)-pteridinone
MS: APCI (+ve) 421 (M+1).

EXAMPLE 68
(S)-2-[(2,3-difluorobenzyl)thio]-4-{[1-(hydroxymethyl)-2,2-dimethylpropyl]amino}-7(8H)-pteridinone
MS: APCI (+ve) 422 (M+1).

EXAMPLE 69
(R)-2-[(2,3-difluorobenzyl)thio]-4-{[1-(hydroxymethyl)-3-methylbutyl]amino}-7(8H)-pteridinone
MS: APCI (+ve) 422 (M+1).

EXAMPLE 70
2-[(2,3-difluorobenzyl)thio]-4-[(6-hydroxyhexyl)amino]-7(8H)-pteridinone
MS: APCI (+ve) 422 (M+1).

EXAMPLE 71
2-[(2,3-difluorobenzyl)thio]-4-{[3-(dimethylamino)-2,2-dimethylpropyl]amino}-7(8H)-pteridinone
MS: APCI (+ve) 436 (M+1).

EXAMPLE 72
(S)-ethyl 2-({2-[(2,3-difluorobenzyl)thio]-7-oxo-7,8-dihydro-4-pteridinyl}amino)-3-hydroxypropanoate
MS: APCI (+ve) 438 (M+1).

Pharmacological Data
Ligand Binding Assay

[$^{125}$I]IL-8 (human, recombinant) was purchased from Amersham, U.K. with a specific activity of 2,000 Ci/mmol. All other chemicals were of analytical grade. High levels of hrCXCR2 were expressed in HEK 293 cells (human embryo kidney 293 cells ECACC No. 85120602) (Lee et al. (1992) *J. Biol. Chem.* 267 pp16283–16291). hrCXCR2 cDNA was amplified and cloned from human neutrophil mRNA. The DNA was cloned into PCRScript (Stratagene) and clones were identified using DNA. The coding sequence was subcloned into the eukaryotic expression vector RcCMV (Invitrogen). Plasmid DNA was prepared using Quiagen Megaprep 2500 and transfected into HEK 293 cells using Lipofectamine reagent (Gibco BRL). Cells of the highest expressing clone were harvested in phosphate-buffered saline containing 0.2% (w/v) ethylenediaminetetraacetic acid (EDTA) and centrifuged (200 g, 5 min.). The cell pellet was resuspended in ice cold homogenisation buffer [10 mM HEPES (pH 7.4), 1 mM dithiothreitol, 1 mM EDTA and a panel of protease inhibitors (1 mM phenyl methyl sulphonyl fluoride, 2μg/ml soybean trypsin inhibitor, 3 mM benzamidine, 0.5 μl/ml leupeptin and 100 μg/ml bacitracin)] and the cells left to swell for 10 minutes. The cell preparation was disrupted using a hand held glass mortar/PTFE pestle homogeniser and cell membranes harvested by centrifuigation (45 minutes, 100,000 g, 4° C.). The membrane preparation was stored at −70° C. in homogenisation buffer supplemented with Tyrode's salt solution (137 mM NaCl, 2.7mM KCl, 0.4 mM NaH$_2$PO$_4$), 0.1% (w/v) gelatin and 10% (v/v) glycerol.

All assays were performed in a 96-well MultiScreen 0.45 μm filtration plates (Millipore, U.K.). Each assay contained ~50 pM [$^{125}$I]IL-8 and membranes (equivalent to ~200,000 cells) in assay buffer [Tyrode's salt solution supplemented with 10 mM HEPES (pH 7.4), 1.8 mM CaCl$_2$, 1 mM MgCl$_2$, 0.125 mg/ml bacitracin and 0.1% (w/v) gelatin]. In addition, a compound of formula (I) according to the Examples was pre-dissolved in DMSO and added to reach a final concentration of 1% (v/v) DMSO. The assay was initiated with the addition of membranes and after 1.5 hours at room temperature the membranes were harvested by filtration using a Millipore MultiScreen vacuum manifold and washed twice with assay buffer (without bacitracin). The backing plate was removed from the MultiScreen plate assembly, the filters dried at room temperature, punched out and then counted on a Cobra γ-counter.

The compounds of formula (I) according to the Examples were found to have IC$_{50}$ values of less than (<) 10 μM.

Intracellular Calcium Mobilisation Assay

Human neutrophils were prepared from EDTA-treated peripheral blood, as previously described (Baly et al. (1997) Methods in Enzymology 287 pp70–72), in storage buffer [Tyrode's salt solution (137 mM NaCl, 2.7 mM KCl, 0.4 mM NaH$_2$PO$_4$) supplemented with 5.7 mM glucose and 10 mM HEPES (pH 7.4)].

The chemokine GROα (human, recombinant) was purchased from R&D Systems (Abingdon, U.K.). All other chemicals were of analytical grade. Changes in intracellular free calcium were measured fluorometrically by loading neutrophils with the calcium sensitive fluorescent dye, fluo-3,as described previously (Merritt et al. (1990) Biochem. J. 269,pp513–519). Cells were loaded for 1 hour at 37° C. in loading buffer (storage buffer with 0.1% (w/v) gelatin) containing 5 μM fluo-3 AM ester, washed with loading buffer and then resuspended in Tyrode's salt solution supplemented with 5.7 mM glucose, 0.1% (w/v) bovine serum albumin (BSA), 1.8 mM CaCl$_2$ and 1 mM MgCl$_2$. The cells were pipetted into black walled, clear bottom, 96 well micro plates (Costar, Boston, U.S.A.) and centrifuged (200 g, 5 minutes, room temperature).

A compound of formula (I) according to the Examples was pre-dissolved in DMSO and added to a final concentration of 0.1% (v/v) DMSO. Assays were initiated by the addition of an Aso concentration of GROα and the transient increase in fluo-3 fluorescence ($\lambda_{Ex}$=490 nm and $\lambda_{Em}$=520 nm) monitored using a FLIPR (Fluorometric Imaging Plate Reader, Molecular Devices, Sunnyvale, U.S.A.).

The compounds of formula (I) according to the Examples were tested and found to be antagonists of the CXCR2 receptor in human neutrophils.

What is claimed is:
1. A compound of formula (I) or a pharmaceutically acceptable salt:

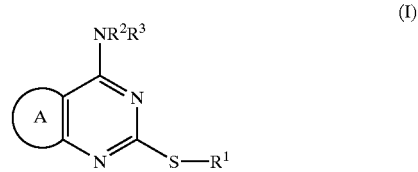
(I)

in which:
A is a group of formula (b):

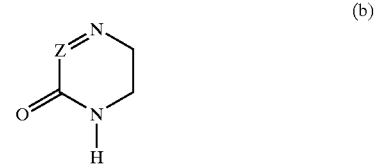
(b)

R$^1$ represents a C$_3$–C$_7$ carbocyclic, C$_1$–C$_8$ alkyl, C$_2$–C$_6$ alkenyl or C$_2$–C$_6$ alkynyl group, the latter four groups being optionally substituted by one or more substituent groups independently selected from halogen atoms, —OR$^4$, —NR$^5$R$^6$, —CONR$^5$R$^6$, —COOR$^7$, —NR$^8$COR$^9$, —SR$^{10}$, —SO$_2$R$^{10}$, —SO$_2$NR$^5$R$^6$, —NR$^8$SO$_2$R$^{10}$, an aryl or heteroaryl group both of which can be optionally substituted by one or more substituents independently selected from halogen atoms, cyano, nitro, —OR$^4$, —NR$^5$R$^6$, —CONR$^5$R$^6$, —COOR$^7$, —NR$^8$COR$^{10}$, —SR$^{10}$, —SO$_2$R$^{10}$, —SO$_2$NR$^5$R$^6$, —NR$^8$SO$_2$R$^{10}$, C$_1$–C$_6$ alkyl or trifluoromethyl groups; wherein aryl is selected from the group consisting of phenyl and naphthyl, and heteroaryl is selected from the group consisting of pyridine, pyrimidine, thiazole, oxazole, pyrazole, imidazole, and furan one of R$^2$ and R$^3$ is hydrogen and the other is C$_3$–C$_4$ alkyl substituted by one or more hydroxy groups;

R$^4$ represents hydrogen, C$_1$–C$_6$ alkyl or a phenyl group the latter two of which may be optionally substituted by one or more substituent groups independently selected from halogen atoms, phenyl, —OR$^{11}$ and —NR$^{12}$R$^{13}$;

R$^5$ and R$^6$ independently represent a hydrogen atom or a C$_1$–C$_6$ alkyl or phenyl group the latter two of which may be optionally substituted by one or more substituent groups independently selected from halogen atoms, phenyl, —OR$^{14}$ and —NR$^{15}$R$^{16}$, —CONR$^{15}$R$^{16}$, —NR$^{15}$COR$^{16}$, —SO$_2$NR$^{15}$R$^{16}$, NR$^{15}$SO$_2$R$^{16}$ or R$^5$ and R$^6$ together with the nitrogen atom to which they are attached form a 4- to 7-membered saturated heterocyclic ring system optionally comprising a further heteroatom selected from oxygen and nitrogen atoms, which ring system may be optionally substituted by one or more substituent groups independently selected from phenyl, —OR$^{14}$, —COOR$^{14}$, —NR$^{15}$R$^{16}$, —CONR$^{15}$R$^{16}$, —NR$^{15}$COR$^{16}$, —SO$_2$NR$^{15}$R$^{16}$, NR$^{15}$SO$_2$R$^{16}$ or C$_1$–C$_6$ alkyl, itself optionally substituted by one or more substituents independently selected from halogen atoms and —NR$^{15}$R$^{16}$ and —OR$^{17}$ groups;

R$^{10}$ represents a C$_1$–C$_6$ alkyl or a phenyl group, each of which may be optionally substituted by one or more substituent groups independently selected from halogen atoms, phenyl, —OR$^{17}$ and —NR$^{15}$R$^{16}$;

Z is CR$^{20}$ where R$^{20}$ represents H; and each of R$^7$, R$^8$, R$^9$, R$^{11}$, R$^{12}$, R$^{13}$, R$^{14}$, R$^{15}$, R$^{16}$ and R$^{17}$ independently represent a hydrogen atom, C$_1$–C$_6$ alkyl, or a phenyl group.

2. A compound according to claim 1, wherein R$^1$ represents an optionally substituted benzyl group.

3. A compound according to claim 1, wherein one of R$^2$ and R$^3$ is hydrogen and the other is C$_3$–C$_4$ alkyl substituted by one or more hydroxy groups.

4. A compound according to claim 1, wherein one of R$^2$ and R$^3$ is hydrogen and the other is CH(CH$_3$)CH$_2$OH, CH(Et)CH$_2$OH, C(CH$_3$)$_2$CH$_2$OH or CH(CH$_2$OH)$_2$.

5. A compound according to claim 1, wherein one of R$^2$ and R$^3$ is hydrogen and the other is CH(CH$_3$)CH$_2$OH.

6. A compound according to claim 3, in the form of the (R) isomer.

7. A compound according to claim 1 selected from:

2-[[(2,3-Difluorophenyl)methyl]thio]-4-[[(1R)-2-hydroxy-1-methylethyl]amino]-7(8H)-pteridinone 2-[[(2,3-Difluorophenyl)methyl]thio]-4-[[2-hydroxy-1-(hydroxymethyl)ethyl]amino]-7(8H)-pteridinone 2-[[(2,3-Difluorophenyl)methyl]thio]-4-[(2-hydroxyethyl)amino]-7(8H)-pteridinone (2R)-2-[[2-[[2,3-Difluorophenyl)methyl]thio]-7,8-dihydro-7-oxo-4-pteridinyl]amino]-propanamide 2-[[(3-Chloro-2-fluorophenyl)methyl]thio]-4-[[(1R)-2-hydroxy-1-methylethyl]amino]-7(8H)-pteridinone 2-[[(3-Chloro-2-fluorophenyl)methyl]thio]-4-[(2-hydroxyethyl)amino]-7(8H)-pteridinone 2-[[(3-Chloro-2-fluorophenyl)methyl]thio]-4-[[2-hydroxy-1-(hydroxymethyl)ethyl]amino]-7(8H)-pteridinone

[(2R)-2-[[2-[[(3-Chloro-2-fluorophenyl)methyl]thio]-7,8-dihydro-7-oxo-4-pteridinyl]amino]propyl]-carbamic acid, 1,1-dimethylethyl ester 4-[[(1R)-2-Amino-1-methylethyl]amino]-2-[[(3-chloro-2-fluorophenyl)methyl]thio]-7(8H)-pteridinone, monohydrochloride 2-[[(3-Chloro-4-methoxyphenyl)methyl]thio]-4-[[2-hydroxy-1-(hydroxymethyl)ethyl]amino]-7(8H)-pteridinone 4-[(2-Aminoethyl)amino]-2-[[(3-chloro-4-methoxyphenyl)methyl]thio]-7(8H)-pteridinone, monotrifluoroacetate 2-[[(2-Fluoro-4-methoxyphenyl)methyl]thio]-4-[[(1R)-2-hydroxy-1-methylethyl]amino]-7(8H)-pteridinone 2-[[(2-Fluoro-3-methylphenyl)methyl]thio]-4-[[(1R)-2-hydroxy-1-methylethyl]amino]-7(8H)-pteridinone 2-[[(3-Fluoro-2-methoxyphenyl)methyl]thio]-4-[[(1R)-2-hydroxy-1-methylethyl]amino]-7(8H)-pteridinone 2-[[[4-(Difluoromethoxy)phenyl]methyl]thio]-4-[[(1R)-2-hydroxy-1-methylethyl]amino]-7(8H)-pteridinone 4-[[(1R)-2-Hydroxy-1-methylethyl]amino]-2-[[(4-hydroxyphenyl)methyl]thio]-7(8H)-pteridinone 4-[[(1R)-2-Hydroxy-1-methylethyl]amino]-2-[[(3-methylphenyl)methyl]thio]-7(8H)-pteridinone 2-[(1,3-Benzodioxol-4-ylmethyl)thio]-4-[[(1R)-2-hydroxy-1-methylethyl]amino]-7(8H)-pteridinone 2-[[(2,4-Difluorophenyl)methyl]thio]-4-[[(1R)-2-hydroxy-1-methylethyl]amino]-7(8H)-pteridinone 2-[[(3-Chlorophenyl)methyl]thio]-4-[[(1R)-2-hydroxy-1-methylethyl]amino]-7(8H)-pteridinone 4-[[(1R)-2-Hydroxy-1-methylethyl]amino]-2-[(5-isoxazolylmethyl)thio]-7(8H)-pteridinone 4-[[-2-Hydroxy-1-(hydroxymethyl)ethyl]amino]-2-[(5-isoxazolylmethyl)thio]-7(8H)-pteridinone 4-[[(1R)-2-Hydroxy-1-methylethyl]amino]-2-[[(5-methyl-2-furanyl)methyl]thio]-7(8H)-pteridinone 2-[[(2-Fluorophenyl)methyl]thio]-4-[[(1R)-2-hydroxy-1-methylethyl]amino]-7(8H)-pteridinone 4-[[(1R)-2-Hydroxy-1-methylethyl]amino]-2-[[(2-thienyl)methyl]thio]-7(8H)-pteridinone 2-[[(2-Fluorophenyl)methyl]thio]-4-[[-2-hydroxy-1-(hydroxymethylethyl]amino]-7(8H)-pteridinone 4-[[-2-Hydroxy-1-(hydroxymethyl)ethyl]amino]-2-[(2-thienylmethyl)thio]-7(8H)-pteridinone 2-[[(2-Fluoro-5-methylphenyl)methyl]thio]-4-[[(1R)-2-hydroxy-1-methylethyl]amino]-7(8H)-pteridinone 2-[[(2-Fluoro-3-(trifluoromethyl)phenyl)methyl]thio]-4-[[(1R)-2-hydroxy-1-methylethyl]amino]-7(8H)-pteridinone 2-[[(2-Fluoro-3-(trifluoromethyl)phenyl)methyl]thio]-4-[[2-hydroxy-1-(hydroxymethyl)ethyl]amino]-7(8H)-pteridinone 2-[[(2-Fluoro-3-(trifluoromethyl)phenyl)methyl]thio]-4-[(2-hydroxyethyl)amino]-7(8H)-pteridinone 4-[(2-aminoethyl)amino]-2-[[(2-fluoro-3-(trifluoromethyl)phenyl)methyl]thio]-7(8H)-pteridinone 2-[[(2,3-Difluorophenyl)methyl]thio]-4-[[2-hydroxy-1-(hydroxymethyl)-1-methylethyl]amino]-7(8H)-pteridinone 2-[[(2,3-Difluorophenyl)methyl]thio]-4-[[(1R)-2-hydroxy-1-methylethyl]amino]-7(8H)-pteridinone sodium salt 2-[(2,3-difluorobenzyl)thio]-4-(ethylamino)-7(8H)-pteridinone 2-[(2,3-difluorobenzyl)thio]-4-(isopropylamino)-7(8H)-pteridinone (+/−)-4-(sec-butylamino)-2-[(2,3-difluorobenzyl)thio]-7(8H)-pteridinone 2-({2-[(2,3-difluorobenzyl)thio]-7-oxo-7,8-dihydro-4-pteridinyl}amino)acetamide (+/−)-2-[(2,3-difluorobenzyl)thio]-4-[(2-hydroxypropyl)amino]-7(8H)-pteridinone (S)-2-[(2,3-difluorobenzyl)thio]-4-[(2-hydroxy-1-methylethyl)amino]-7(8H)-pteridinone (+/−)-2-[(2,3-difluorobenzyl)thio]-4-[(2-hydroxy-1-methylethyl)amino]-7(8H)-pteridinone (R)-2-[(2,3-difluorobenzyl)thio]-4-[(2-hydroxypropyl)amino]-7(8H)-pteridinone 2-[(2,3-difluorobenzyl)thio]-4-[(3-hydroxypropyl)amino]-7(8H)-pteridinone 2-[(2,3-difluorobenzyl)thio]-4-[(2-hydroxyethyl)(methyl)amino]-7(8H)-pteridinone 3-[{2-[(2,3-difluorobenzyl)thio]-7-oxo-7,8-dihydro-4-pteridinyl}(methyl)amino]propanenitrile (R)-2-[(2,3-difluorobenzyl)thio]-4-{[1-(hydroxymethyl)propyl]amino}-7(8H)-pteridinone (R)-2-[(2,3-difluorobenzyl)thio]-4-{[1-(hydroxymethyl)propyl]amino}-7(8H)-pteridinone 2-[(2,3-difluorobenzyl)thio]-4-[(4-hydroxybutyl)amino]-7(8H)-pteridinone (+/−)-2-[(2,3-difluorobenzyl)thio]-4-{[1-(hydroxymethyl)propyl]amino}-7(8H)-pteridinone 2-[(2,3-difluorobenzyl)thio]-4-[(2-hydroxy-1,1-dimethylethyl)amino]-7(8H)-pteridinone 2-[(2,3-difluorobenzyl)thio]-4-[ethyl(2-hydroxyethyl)amino]-7(8H)-pteridinone (+/−)-4-[(3-amino-2-hydroxypropyl)amino]-2-[(2,3-difluorobenzyl)thio]-7(8H)-pteridinone (+/−)-2-[(2,3-difluorobenzyl)thio]-4-[(1,3-dimethylbutyl)amino]-7(8H)-pteridinone (1R,2R)-2-[(2,3-difluorobenzyl)thio]-4-[(2-hydroxycyclopentyl)amino]-7(8H)-pteridinone 2-[(2,3-difluorobenzyl)thio]-4-[(5-hydroxypentyl)amino]-7(8H)-pteridinone (+/−)-2-[(2,3-difluorobenzyl)thio]-4-{[1-(hydroxymethyl)butyl]amino}-7(8H)-pteridinone (+/−)-methyl 2-({2-[(2,3-difluorobenzyl)thio]-7-oxo-7,8-dihydro-4-pteridinyl}amino)propanoate 2-[(2,3-difluorobenzyl)thio]-4-[(3-hydroxy-2,2-dimethylpropyl)amino]-7(8H)-pteridinone (1R,2R)-2-[(2,3-difluorobenzyl)thio]-4-{[2-hydroxy-1-(hydroxymethyl)propyl]amino}-7(8H)-pteridinone 4-[bis(2-hydroxyethyl)amino]-2-[(2,3-difluorobenzyl)thio]-7(8H)-pteridinone 2-[(2,3-difluorobenzyl)thio]-4-{[2-(2-hydroxyethoxy)ethyl]amino}-7(8H)-pteridinone 2-[(2,3-difluorobenzyl)thio]-4-[(2,2-dimethoxyethyl)amino]-7(8H)-pteridinone 4-{[2-(diethylamino)ethyl]amino}-2-[(2,3-difluorobenzyl)thio]-7(8H)-pteridinone (S)-2-[(2,3-difluorobenzyl)thio]-4-{[1-(hydroxymethyl)-2,2-dimethylpropyl]amino}-7(8H)-pteridinone (R)-2-[(2,3-difluorobenzyl)thio]-4-{[1-(hydroxymethyl)-3-methylbutyl]amino}-7(8H)-pteridinone 2-[(2,3-difluorobenzyl)thio]-4-{[3-(dimethylamino)-2,2-dimethylpropyl]amino}-7(8H)-pteridinone (S)-ethyl 2-({2-[(2,3-difluorobenzyl)thio]-7-oxo-7,8-dihydro-4-pteridinyl}amino)-3-hydroxypropanoate and their pharmaceutically acceptable salts.

\* \* \* \* \*